(12) United States Patent
Barreca et al.

(10) Patent No.: US 10,407,456 B2
(45) Date of Patent: Sep. 10, 2019

(54) NUCLEOSIDE PHOSPHORAMIDATES USEFUL FOR THE TREATMENT OF VIRAL INFECTIONS AND PREPARATION THEREOF

(71) Applicant: QUIMICA SINTETICA, S.A., Barcelona (ES)

(72) Inventors: Giuseppe Barreca, Montevecchia (IT); Marcello Rasparini, Mol (BE); Andrea Poggiali, Caronno Pertusella (IT); Luca Carcone, Milan (IT); Roberto Rocco Tufaro, Sozzago (IT); Giovanni Marras, Galliate (IT); Maurizio Taddei, Monteriggioni (IT); Elena Cini, Gambassi Terme (IT)

(73) Assignee: QUIMICA SINTETICA, S.A., Barcelona (ES)

( * ) Notice: Subject to any disclaimer, the term of this patent is extended or adjusted under 35 U.S.C. 154(b) by 0 days.

(21) Appl. No.: 15/560,862

(22) PCT Filed: Mar. 25, 2016

(86) PCT No.: PCT/IB2016/051710
§ 371 (c)(1),
(2) Date: Sep. 22, 2017

(87) PCT Pub. No.: WO2016/151542
PCT Pub. Date: Sep. 29, 2016

(65) Prior Publication Data
US 2018/0118776 A1 May 3, 2018

(30) Foreign Application Priority Data

Mar. 26, 2015 (IT) .......................... 102015000009877
Jul. 13, 2015 (IT) .......................... 102015000033419

(51) Int. Cl.
*C07H 19/10* (2006.01)
*C07H 1/00* (2006.01)
*C07H 19/06* (2006.01)
*C07H 1/02* (2006.01)

(52) U.S. Cl.
CPC ............... *C07H 19/10* (2013.01); *C07H 1/00* (2013.01); *C07H 1/02* (2013.01); *C07H 19/06* (2013.01)

(58) Field of Classification Search
None
See application file for complete search history.

(56) References Cited

FOREIGN PATENT DOCUMENTS

| WO | 2008121634 A2 | 10/2008 |
|----|---------------|---------|
| WO | 2010135569 A1 | 11/2010 |
| WO | 2011123645 A2 | 10/2011 |
| WO | 2012040126 A1 | 3/2012 |
| WO | 2014076490 A1 | 5/2014 |

OTHER PUBLICATIONS

Jong Hyun Cho, et al., Tetrahedron, 67:30:5487-5493 (2011);.
Green et al, *Protective Groups in Organix Synthesis*, pp. 61-99,113-178, 520-522, 532-534, 574-581 (3$^{rd}$ ed. 1999).
Green et al, Protective Groups in Organic Synthesis, pp. 61-99, 113-178, 520-522,532-534, 574-581 (3$^{rd}$ 1999).
Cho et al., "Efficient synthesis of nucleoside aryloxy phosphoramidate prodrugs utilizig benzyloxycarbonyl protection," Tetrahedron, 67:5487-5493 (2011).
International Search Report of PCT/IB2016/051710 dated Jul. 7, 2016.

*Primary Examiner* — Layla D Berry
(74) *Attorney, Agent, or Firm* — Abelman, Frayne & Schwab

(57) ABSTRACT

Two processes are described for preparing, in different diastereomeric purity degrees, the compound (S)-isopropyl-2-(((S)-(((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)-phosphoryl)amino) propanoate, having the formula given below, known as Sofosbuvir and used for the treatment of hepatitis C.

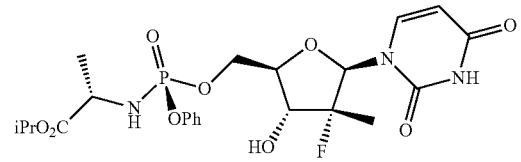

13 Claims, No Drawings

NUCLEOSIDE PHOSPHORAMIDATES USEFUL FOR THE TREATMENT OF VIRAL INFECTIONS AND PREPARATION THEREOF

RELATED APPLICATIONS

This application is a national phase of International Application No. PCT/IB2016/051710 filed Mar. 25, 2016, and claims priority from Italian Patent Application Nos. 102015000009877 filed Mar. 26, 2015 and 102015000033419 filed Jul. 13, 2015, ail incorporated by reference in their entirety.

FIELD OF THE INVENTION

The present invention relates to an industrially applicable and advantageous process for the preparation of phosphoramidates useful for the treatment of viral infections, or of intermediates useful for the preparation thereof.

BACKGROUND ART

Hepatitis C virus (HCV) is a member of the family Flaviviridae. It is a virus provided with a viral envelope having a mainly lipid composition and a icosahedral capsid containing a single-stranded RNA molecule about 9,600 nucleotide base long encoding a single polyprotein containing 3,000 amino acids. In the polyprotein, which is processed by viral and cellular proteases, at least 10 distinct viral proteins can be identified which are critical for the replication and assembly of the viral progeny.

According to estimates by the World Health Organization, hepatitis C-infected people in the world are about 200 millions, with an annual increase of about 3 or 4 millions.

The compound (S)-isopropyl-2-(((S)-(((2R,3R,4R,5R)-5-(2,4-dioxo-3,4-dihydropyrimidin-1 (2H)-yl)-4-fluoro-3-hydroxy-4-methyltetrahydrofuran-2-yl)methoxy)(phenoxy) phosphoryl)amino) propanoate, known as Sofosbuvir, is a prodrug used to treat hepatitis C. Its main metabolite, 2'-deoxy-2'-α-fluoro-β-C-methyluridine-5'-monophosphate, inhibits RNA polymerase that the hepatitis C virus uses to replicate its RNA. This compound has the following structural formula:

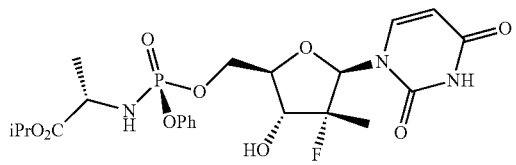

Sofosbuvir and other similar compounds were first described in the international patent application WO 20081121634 A2. This application describes a process comprising a phosphorylation of nucleoside (B) with phosphorus chloride (A) in the presence of N-methylimidazole followed by preparative chromatographic purification to give Sofosbuvir as a mixture of phosphorus diastereoisomers, according to the following scheme:

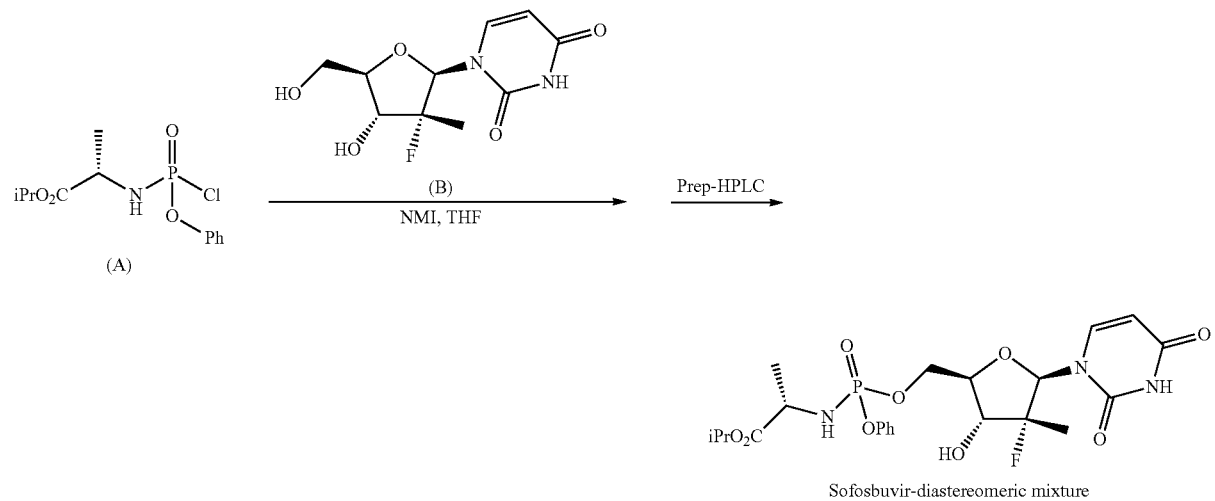

Sofosbuvir-diastereomeric mixture

Said mixture is then purified by chromatography on chiral stationary phase to give Sofosbuvir in a diastereomerically purified form.

Two different chromatography separations make this process non-industrializable. An ameliorative process for the preparation of Sofosbuvir is described in the international application WO 2010/135569 A1. This patent application describes two possible routes for the preparation of the diastereomerically purified form of Sofosbuvir. The first involves the phosphorylation of nucleoside (B) with phosphochloride (A) in the presence of N-methylimidazole to give a mixture of products (C), (D) and (E). This mixture is treated with tert-butyldimethylsilyl chloride in order to selectively protect the hydroxyl in position 5' of compound (E) and purified by chromatography to give Sofosbuvir diastereomericaliy mixed with the phosphorous, which is finally converted into the diastereomerically purified form by crystallization:

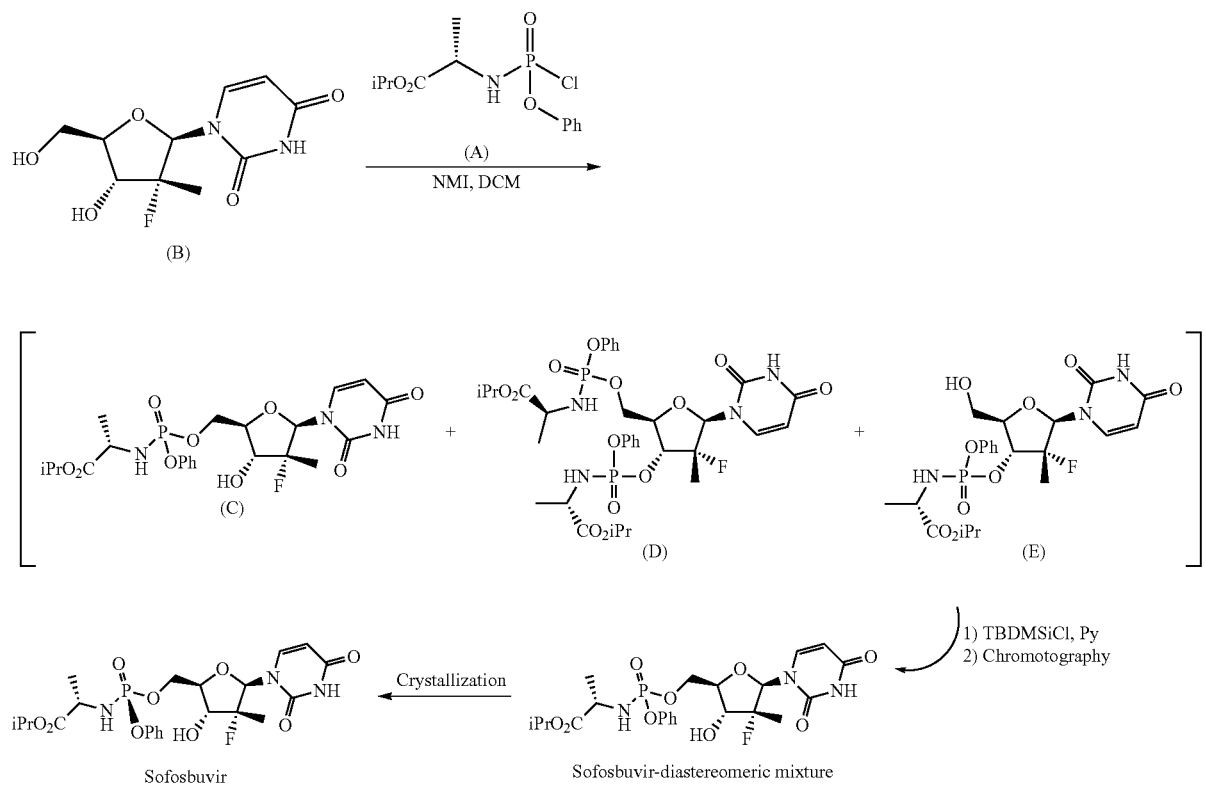

Drawbacks of this route derive from the poor selectivity of the phosphorylation reaction and from the need to derivatize the reaction mixture with tert-butyldimethylsilyl chloride to make (inter alia by chromatography, a poorly industrializable technique) the compound of interest cleavable.

The second approach involves the conversion of (A) into the diastereoisomeric mixture of phosphoramidates (L). The desired diastereomer (H) is isolated by fractional crystallization and then condensed with a protected nucleoside (F) to give a protected form of Sofosbuvir (G) which is converted into the latter by treatment with sodium sulfite and sodium metabisulfite.

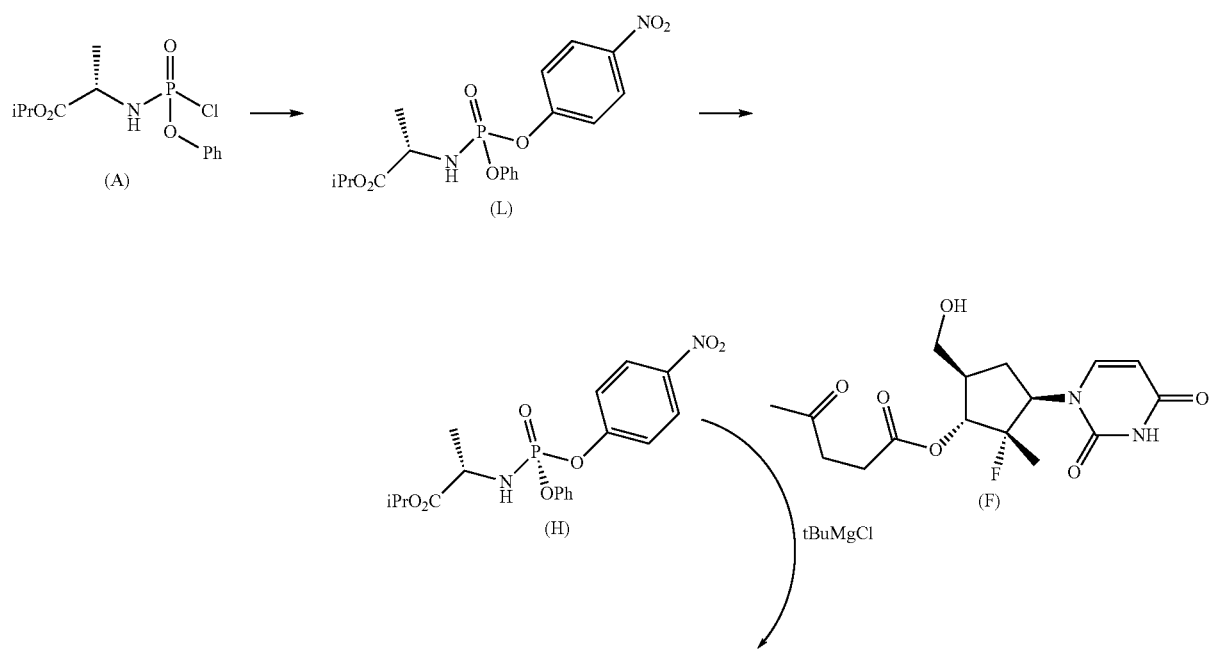

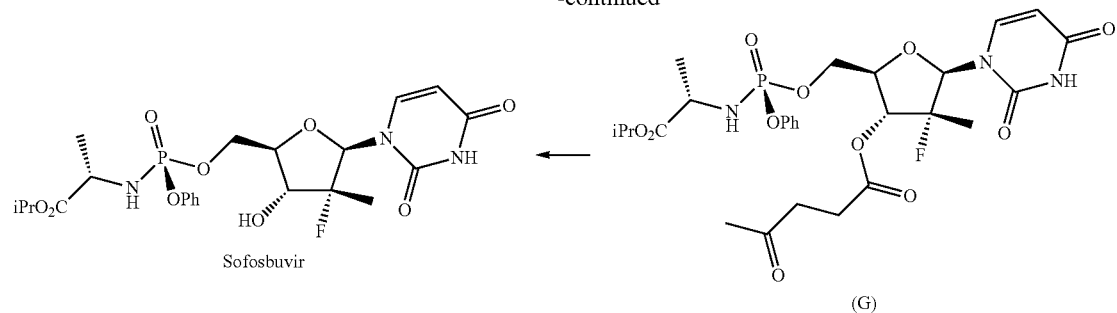

Sofosbuvir

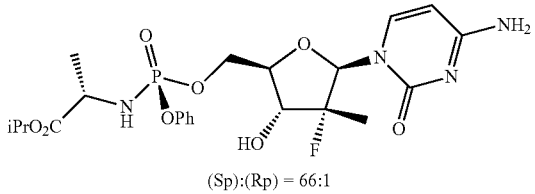

(G)

A further method for the preparation of Sofosbuvir in the form of diastereomeric mixture is described in *Tetrahedron* (2011), 67, 5487-5493 and involves the treatment of a protected nucleoside (I) with phosphochloride (A) in the presence of N-methylimidazole and subsequent hydrogenolysis of the protecting group in position 3':

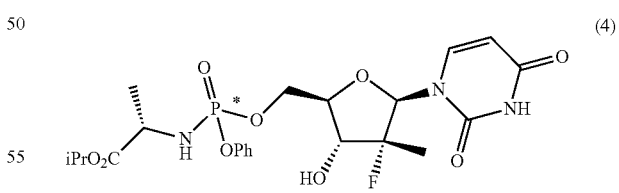

(Sp):(Rp) = 66:1

Although potentially advantageous, this procedure is affected by very poor conversions (20% as mentioned in example 47).

The object of the present invention is to provide a method for the synthesis of Sofosbuvir, which is carried out with high yields, in a small number of synthesis steps and which provides the desired products with suitable purity for pharmaceutical use.

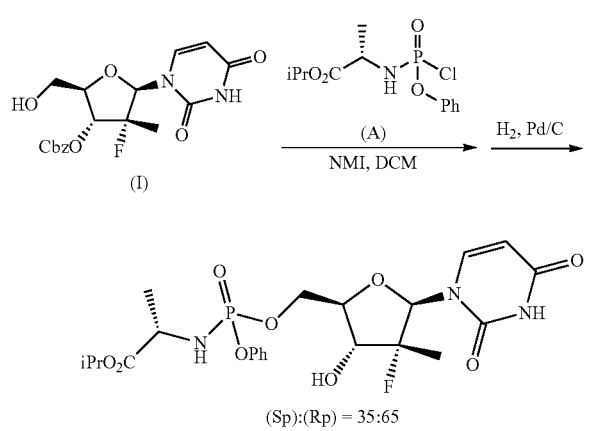

(Sp):(Rp) = 35:65

However, the process described leads to the formation of a mixture of about 35:65 diastereoisomers in which (Sp)-Sofosbuvir (the compound of interest) is the minority component and from which the isolation of the latter by crystallization is not actually feasible.

Finally, the international application WO 2014/076490 A1 describes the preparation of an enriched mixture of the two phosphorus diastereoisomers of Sofosbuvir by treating phosphochloride (A) with a nucleoside (M) in the presence of a metal salt selected from copper, iron, lanthanum and ytterbium.

SUMMARY OF THE INVENTION

These objects are achieved with the present invention which, in a first aspect thereof, relates to a process for preparing a diastereomerically enriched mixture of the nucleoside phosphoramidate (4):

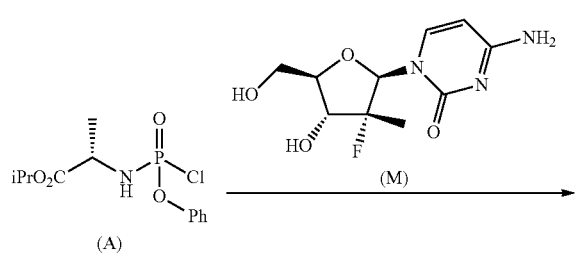

(4)

said process comprising the following synthesis steps:

a) phosphorylating the nucleoside (2) with a phosphoramidate (1) in the presence of an organolithium reagent, an organomagnesium reagent or a mixture thereof, or of a sodium, lithium, potassium or magnesium amide at a temperature of between −60 and 0° C. in a solvent or a mixture of ethereal solvents:

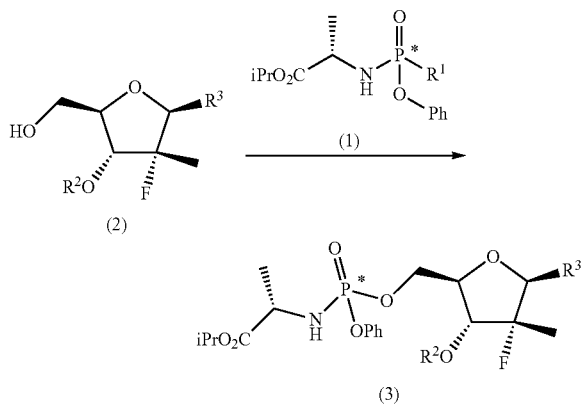

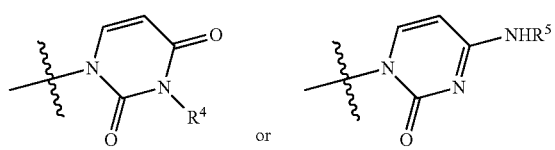

wherein:
$R^1$ is chlorine, bromine, a sulfonate of formula —OSO2R$^8$ or camphorsulfonate;
$R^2$ is an alcohol protecting group selected from carbonates or ethers;
$R^3$ is or N

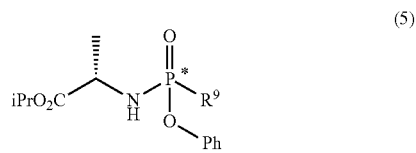

$R^4$ is hydrogen or an amine protecting group;
$R^5$ is hydrogen or an amine protecting group; and
$R^8$ is C1-C4 alkyl, aryl or aryl substituted with a C1-C4 alkyl, a halogen or a nitro group;
b) converting the nucleoside phosphoramidate (3) into the diastereomerically enriched mixture of the nucleoside phosphoramidate (4):

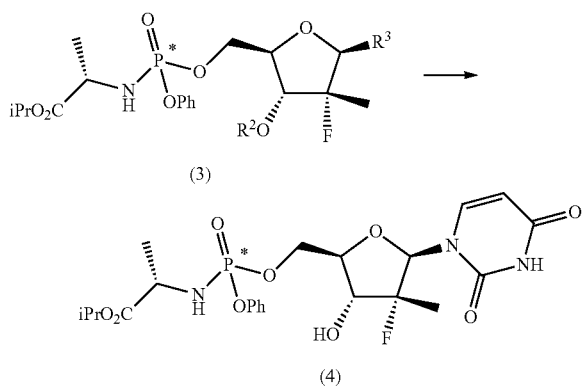

The diastereomerically enriched forms of nucleoside phosphoramidates (4) can be transformed, in an additional and optional step c), in diastereomerically purified mixtures of said phosphoramidates by crystallization from an alkylacetate, from a chlorinated solvent or a mixture thereof with acetonitrile or with an aliphatic hydrocarbon.

Useful alcohol protecting groups are selected from carbonates and ethers and comprise, for example, tert-butoxycarbonyl-(Boc), benzyloxycarbonyl-(Cbz), benzyl, para-methoxybenzyl, allyl, tetrahydropyranyl (THP), 1-ethoxyethyl, methoxymethyl, para-methoxybenzyloxymethyl. Amine protecting groups useful to the invention are, for example, tert-butoxycarbonyl-(Boc), benzyloxycarbonyl-(Cbz), benzyl, para-methoxybenzyl, 2,4-dimethoxybenzyl or 2-hydroxybenzyl. In a second aspect thereof, the present invention relates to a process for the preparation of a diastereomerically purified mixture of the nucleoside phosphoramidate (4) comprising the following synthesis steps:
d) preparing a diastereomerically purified form of the phosphoramidate (5):

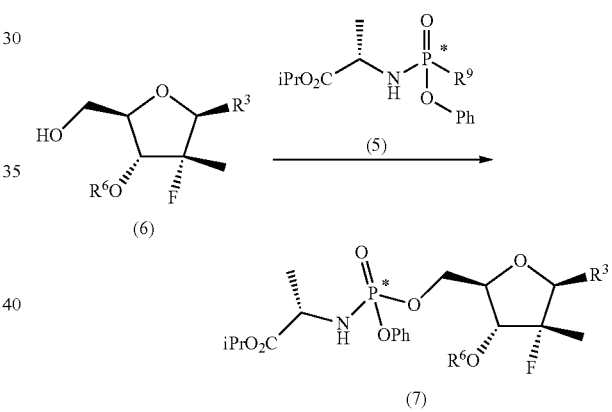

wherein $R^9$ is an aryloxide substituted with at least one electron attractor group;
e) phosphorylating a nucleoside (6) with the diastereomerically purified form of the phosphoramidate (5) in the presence of an organomagnesium reagent and of an alkaline halide, a zinc halide, a copper halide or a mixture thereof:

wherein:
$R^3$ can take any of the above meanings; and
$R^6$ is hydrogen or an alcohol protecting group selected from carbonates or ethers;
f) if $R^8$ is an alcohol protecting group and/or $R^3$ is a protected form of uracil or 4-aminouracil (i.e. $R^4$ and $R^5$ are other than hydrogen), converting the compound of general formula (7) into the diastereomerically purified mixture of the nucleoside phosphoramidate (4).

DETAILED DESCRIPTION OF THE INVENTION

All terms used in this application, unless otherwise indicated, shall be understood in their ordinary meaning as known in the art. More detailed specifications for some of the terms used in this application are listed below and must be applied uniformly to the entire specification and claims, unless otherwise indicated. The symbol ... (dashed bond) present in some of the formulas of the specification and claims indicates that the substituent is directed below the plane of the sheet. The symbol ▬ (wedge bond) present in some of the formulas of the specification and claims indicates that the substituent is directed above the plane of the sheet. In general, the nomenclature used in the present application is based on AUTONOM® v. 4.0, a computerized system of the Beilstein Institute for the assignment of the UPAC systematic nomenclature. In the event of an inconsistency between a structure drawn and the name assigned to said structure, the given formula shall be understood as correct. Moreover, if the stereochemistry of a structure or a portion of the structure is not indicated, for example with a dashed or wedge-shaped bond, such a structure or portion thereof is to be understood as comprising all the stereoisomers thereof.

The compounds prepared by the processes of the present invention have one or more stereocenters, and may exist, be used or be isolated in diastereoisomerically pure forms or as diastereomeric enriched mixtures. It should be understood that the processes of the present invention may yield diastereoisomerically pure forms or diastereomeric enriched mixtures. It should also be understood that the products of the present invention may be isolated as diastereoisomerically pure forms or as diastereomeric enriched mixtures.

The symbol "*" (asterisk) present in some formulas of the specification and the claims indicates a chiral center (asymmetry); however, the absence of asterisks does not necessarily imply that there are no stereocenters in the compound. In particular, when the asterisk is on phosphorus and the molecule contains other stereocenters, the compound in question comprises two diastereoisomers designated as Rp and Sp.

A diastereomeric mixture may contain the two diastereoisomers in any mutual ratio.

The term "diastereomerically enriched" as used in the present application means that one of the diastereoisomers is present in excess of the other diastereoisomer.

The term "diastereomerically purified" refers to a compound whose diastereoisomeric purity is at least 95%, preferably at least 99%.

The first step of the process object of the first aspect of the invention, a), consists in the preparation of a nucleoside phosphoramidate (3) by reaction between a nucleoside (2) (wherein the substituents take the meanings given above) and a phosphoramidate (1) (wherein $R^{1'}$ is chlorine, bromine, a camphorsulfonate or a sulfonate of formula —$OSO_2R^8$, wherein $R^8$ takes one of the meanings given above, for example mesylate (—$OSO_2Me$) or tosylate (pMePhSO_2O—)) in the presence of an organolithium reagent, an organomagnesium reagent or a mixture thereof, or of a sodium, lithium, potassium or magnesium amide at a temperature of between −60 and 0° C. in an ethereal solvent or mixture of solvents:

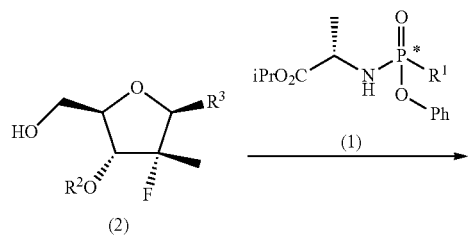

(2)

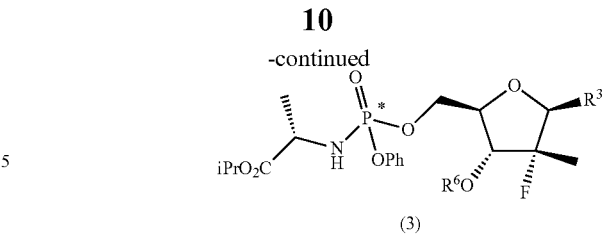

(3)

The nucleoside (2), wherein $R^2$ is a carbonate, may be prepared as described in Tetrahedron (2011), 67, 5487-5493. The nucleoside (2), wherein $R^2$ is an ether, such as allyl or benzyl, may be prepared as described in Carbohydrate Research (2008), 343, 1490-1495.

In particular, the nucleosides of formula (2') or (2"), nucleosides of formula (2) wherein $R^2$ is benzyl, para-methoxybenzyl or allyl, $R^3$ is uracil and $R^4$ is hydrogen, benzyl, para-methoxybenzyl or allyl, may be prepared in an operation j) of the process of the invention, according to two synthesis schemes defined as j.i) and j.ii), respectively.

The synthesis scheme j.i) for the preparation of nucleoside (2') comprises the following synthesis steps:
j.i1) protecting the primary hydroxyl in position 5' of nucleoside (B):

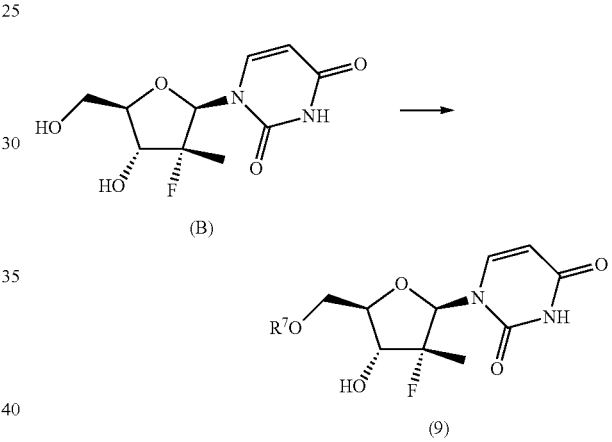

wherein $R^7$ is a protecting group of alcohols orthogonally removable with respect to a benzyl, a para-methoxybenzyl or an allyl, such as a silyl ether or an ester;

j.i.2) selectively protecting the hydroxyl in position 3' of the protected nucleoside (9) to obtain the compound of formula (10):

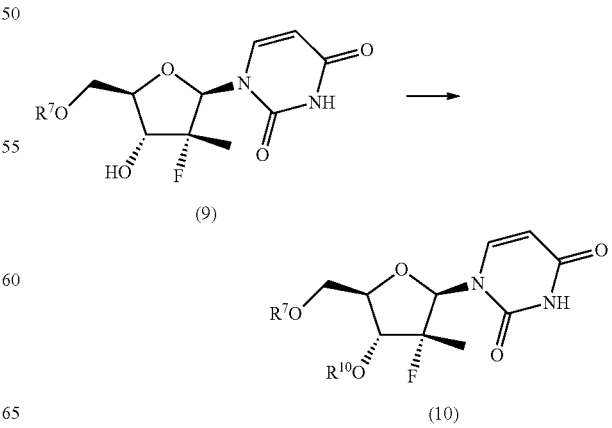

wherein R¹⁰ is a benzyl, a para-methoxybenzyl or an allyl,
j.i.3) removing the protecting group present on the primary hydroxyl in position 5' to obtain a nucleoside of formula (2'):

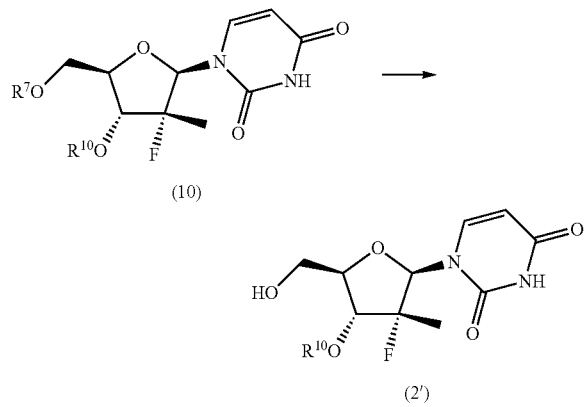

Step j.i.1) comprises the protection of the hydroxyl group in position 5' of nucleoside (B) with a protecting group orthogonally removable with respect to a benzyl, para-methoxybenzyl or allyl ether, such as an ester (preferably benzoate acetate or phenylacetate) or a silyl ether (preferably (trimethylsilyl (TMS), triisopropylsilyl (TIPS), tert-butyldimethylsilyl (TBDMS) or tert-butyldiphenylsilyl (TBDPS)). This step may be conducted according to one of the procedures described in Theodora W. Green, *Protective Groups in Organic Synthesis*, John Wiley & Sons (1999) for the protection of hydroxyls, for example if R⁷ is an ester, according to the conditions described in the same text on page 149-178; and if R⁷ is a silyl ether according to the conditions described in the same text on page 113-147. Such protection conditions are incorporated in the present application by reference.

Step j.i.2) involves selectively protecting the hydroxyl in position 3' of the protected nucleoside (9) to obtain the compound of formula (10). The selective oxygen alkylation reaction is conducted by transforming the protected nucleoside (9) in a reactive form thereof by treatment with a strong base, such as a sodium lithium or potassium alkoxide (preferably methoxide, ethoxide or tert-butoxide); a sodium, lithium or potassium hydride; an amide (preferably sodium, lithium or potassium bis(trimethylsilyl)amides (NaHMDS, LiHMDS or KHMDS) or lithium diisopropylarnide (LDA)) at a temperature of between −30 and 25° C., preferably of between −20 and −10° C., in an ether (preferably tetrahydrofuran), then adding a benzyl, para-methoxybenzyl or allyl halide (preferably a bromide) at a temperature of between −30 and 25° C., preferably of between −20 and −10° C.

The strong base is used in over-stoichiometric amount with respect to the amount of protected nucleoside (9) used; amounts of NaH useful for the purposes of the invention are in the range between 2 and 5 equivalents, preferably in the range between 3 and 4 equivalents.

The benzyl, para-methoxybenzyl or allyl halide is used in a variable amount of between 1 and 2 equivalents with respect to the amount of protected nucleoside (9) used.

The amount of strong base used and the method of adding the benzyl, para-methoxybenzyl or allyl halide cause a greater or lower selectivity towards the formation of the compound of formula (10) than the compound of formula (11) described hereinafter.

Preferably, the strong base is added in subsequent portions.

Step j.i.3) comprises deprotecting the hydroxyl group in position 5' to obtain the nucleoside of formula (2'). This step can be performed according to one of the procedures described in Theodora W. Green, *Protective Groups in Organic Synthesis*, John Wiley & Sons (1999). In particular, if R⁷ is a silyl ether or an ester, said removal conditions, described in the same text on page 113-147 and on page 149-178, respectively, are incorporated in the present application by reference.

The synthesis scheme j.ii) for the preparation of nucleoside (2") comprises the following synthesis steps:

j.ii.1) protecting the hydroxyl in position 5' of nucleoside (B):

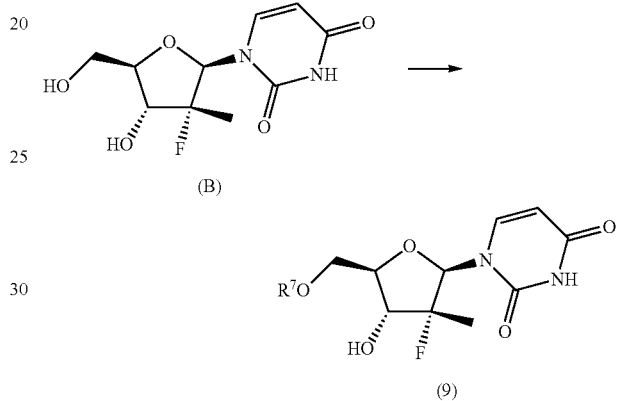

wherein R⁷ is a protecting group of alcohols orthogonally removable with respect to a benzyl, such as a silyl ether or an ester;

j.ii.2) converting the protected nucleoside (9) into the compound of formula (11):

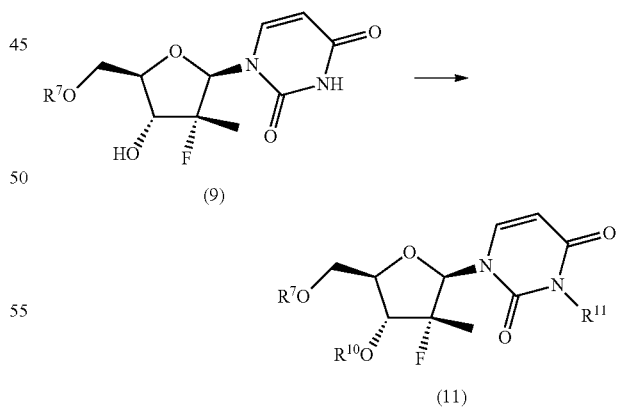

wherein R¹⁰ is a benzyl, a para-methoxybenzyl or an allyl; and

R¹¹ is a benzyl, a para-methoxybenzyl or an allyl, j.ii.3) removing the protecting group present on the primary hydroxyl in position 5' to obtain a nucleoside of formula (2"):

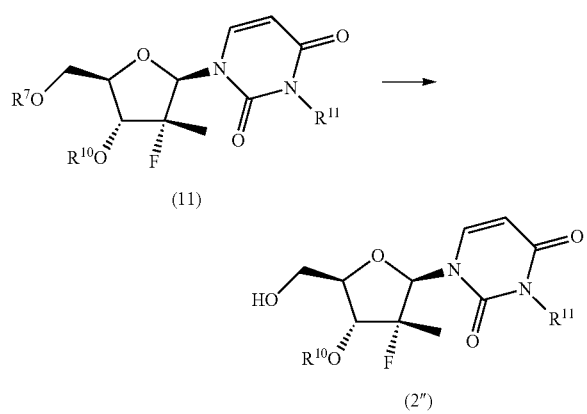

Step j.ii.1) comprises the protection of the hydroxyl group in position 5' of nucleoside (B) with an alcohol protecting group orthogonally removable with respect to a benzyl, such as a silyl ether or an ester. Said operation may be carried out using for example one of the methods described above to perform step j.i.1).

Step j.ii.2) involves the (concurrent or sequential) protection of the hydroxyl in position 5' and of the uracil NH of the protected nucleoside (9) to obtain the compound of formula (11). This step can be performed using one of the methods generally known in the art, such as one of the procedures described in Theodora W. Green, *Protective Groups in Organic Synthesis*, John Wiley & Sons (1999) for the introduction of a benzyl, a para-methoxybenzyl or an allyl. The procedures for preparing said ethers are described in the same text on page 76-86, 86-91 and 61-74, respectively, and are incorporated in the present application by reference. The procedures for preparing the alkylamines are instead described in the same text on page 579-580, 581 and 574-576, respectively, and are incorporated in the present application by reference. Preferably, this operation is carried out by treating the protected nucleoside (9) with a strong base, such as one of those specified above to perform step j.i.2) and then a benzyl, para-methoxybenzyl or allyl halide (preferably bromide) in dimethylformamide, N-methylpyrrolidone, dimethyl acetamide or an ether, such as tetrahydrofuran.

The strong base is used in over-stoichiometric amount with respect to the amount of protected nucleoside (9) used; amounts of NaH useful for the purposes of the invention are in the range between 2 and 5 equivalents, preferably in the range between 3 and 4 equivalents.

The benzyl, para-methoxybenzyl or allyl halide is used in a variable amount of between 1 and 4 equivalents with respect to the amount of protected nucleoside (9) used, preferably in amounts of between 2 and 3 equivalents.

Step j.ii.3), which comprises deprotecting the primary hydroxyl group in position 5' in the compound of formula (11) to obtain the nucleoside of formula (2"), can be performed by using one of the procedures that are generally known in the art, such as one of those described above to perform step j.i.3).

The phosphorylation of nucleoside (2), object of step a) of the process relating to the first aspect of the invention, involves treatment with a phosphoramidate (1), optionally solubilized in an ether (preferably methyl tert-butyl ether) and with an organolithium reagent, an organomagnesium reagent or a mixture thereof, preferably an organomagnesium reagent, or a sodium, lithium or potassium or magnesium amide at a temperature of between −60 and 0° C., for example between −40 and −20° C., in an ether, preferably tetrahydrofuran.

Organolithium reagents useful for this purpose are for example sec-butyllithium or tert-butyllithium; organomagnesium reagents are for example a tert-butyl halide or iso-propylmagnesium, preferably tert-butyl or iso-propylmagnesium chloride; lithium, sodium, potassium or magnesium amides are for example sodium hexamethyldisilazide (NaHMDS), lithium (LiHMDS) or potassium (KHMDS), lithium diisopropylamide (LDA) or magnesium bis(diisopropylamide) (MDA).

If the nucleoside treatment (2) is conducted with an organomagnesium reagent, it is preferably to operate in the presence of an alkali halide (preferably a chloride), for example a lithium, sodium, potassium or cesium chloride, or of a zinc or copper halide.

The amount of phosphoramidate (1) used in the phosphorylation reaction ranges between 1 and 4 equivalents with respect to the amount of nucleoside (2) used, preferably between 2 and 3 equivalents.

The amount of organolithium reagent, organomagnesium reagent or of the mixture thereof used in the phosphorylation reaction ranges between 1 and 4 equivalents with respect to the amount of nucleoside (2) used, preferably between 2 and 3 equivalents.

The amount of lithium, sodium, potassium or magnesium amide used in the phosphorylation reaction ranges between 1 and 3 equivalents with respect to the amount of nucleoside (2) used, preferably 2 equivalents.

The alkaline, zinc or copper halide is used in an amount ranging between 0.5 and 2 equivalents with respect to the amount of organomagnesium used, preferably 1 equivalent.

Preferably, the phosphorylation reaction object of step a) is conducted in a mixture of ethers, for example consisting of tetrahydrofuran and methyl tert-butyl ether.

The second operation, b), of the process of the invention can be carried out according to two alternative synthesis schemes, shown below as b.i), b.ii).

The synthesis scheme b.i) can be performed when $R^3$ is uracil, $R^2$ is an alcohol protecting group selected from carbonates or ethers and $R^4$ is hydrogen, or one of the amine protecting groups specified above, and involves the (concurrent or sequential) deprotection of the hydroxyl group in position 3' and, if R is other than hydrogen, of the uracil nitrogen. In particular, if $R^2$ is a carbonate and/or $R^4$ is a carbamate, the removing conditions are those generally known to the man skilled in the art, such as one of those described in Theodora W. Green, *Protective Groups in Organic Synthesis*, John Wiley & Sons (1999) for removing a tert-butoxycarbonyl- (on page 520-522) and benzyloxycarbonyl- (on page 532-534). Said removing conditions are incorporated in the present application by reference. If, instead, $R^2$ is an ether, preferably benzyl, and/or $R^4$ is a group selected from benzyl, para-methoxybenzyl, 2,4-dimethoxybenzyl or 2-hydroxybenzyl, removing conditions compatible with the invention include for example one of those described in Theodora W. Green, *Protective Groups in Organic Synthesis*, John Wiley & Sons (1999) on page 76-99, which are incorporated in the present application by reference. Preferably, if $R^2$ is a benzyl ether, the deprotection object of step b.i) is conducted by hydrogenolysis.

The synthesis scheme b.ii) can be performed when $R^3$ is 4-aminouracil, $R^2$ is an alcohol protecting group selected from carbonates or ethers and $R^5$ is hydrogen or one of the amine protecting groups specified above, and involves the deprotection of the hydroxyl group in position 3', the conversion of the 4-aminouracil group in uracil and, if $R^5$ is other than hydrogen, the deprotection of said nitrogen. The sequence by which said steps (optionally conducted by isolating the reaction intermediates) may be carried out can be easily determined by a man skilled in the art and preferably takes place according to the following steps:

b.ii.2) converting the compound of general formula (3) into the compound of formula (12):

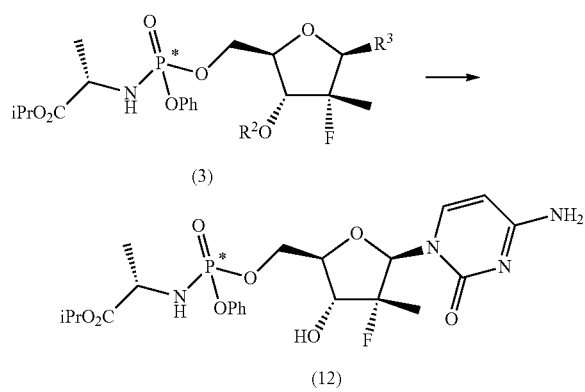

b.ii.2) converting the compound of formula (12) into the diastereomerically enriched mixture of the nucleoside phosphoramidate (4).

Step b.ii.1) involves the conversion of the compound of general formula (3) in the compound of formula (12) by (concurrent or sequential) deprotection of the hydroxyl group in position 3' and/or, if $R^5$ is other than hydrogen, of the amino group of the nitrogenous base. This step can be performed according to one of the techniques known to the man skilled in the art as described above to perform step b.i).

The next step b.ii.2) involves the conversion of the compound of formula (12) into the diastereomerically enriched mixture of the nucleoside phosphoramidate (4), for example by applying the procedure described in the international patent application WO 2008/121634 A2 to convert the compound of formula (B') into nucleoside (B), i.e. treatment with benzoyl chloride, acetic acid and finally ammonia in methanol:

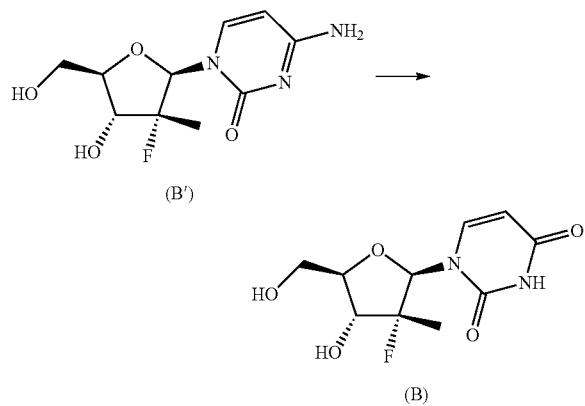

The diastereomerically enriched mixtures of phosphoramidate (4) which can be obtained by the process object of the first aspect of the invention can be transformed, in an additional and optional step c), in diastereomerically purified mixtures of said phosphoramidates by crystallization from an alkylacetate, preferably n-butyl acetate, from a chlorinated solvent, preferably dichloromethane, optionally in a mixture with acetonitrile or with an aliphatic hydrocarbon, preferably heptane.

Phosphoramidates of formula (1) can be prepared according to methods known in the art. In particular, the phosphochloride (A), a phosphoramidate of formula (1), wherein $R^1$ is chlorine, can be prepared in an operation g) according to a process comprising the following synthesis steps:

g.1) preparing the (L)-alanine isopropyl ester hydrochloride (Q):

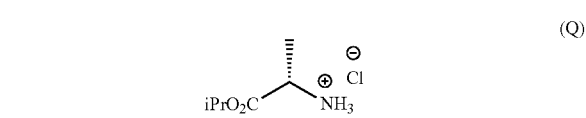

g.2) reacting said hydrochloride (Q) with phenyl dichlorophosphate in the presence of a base:

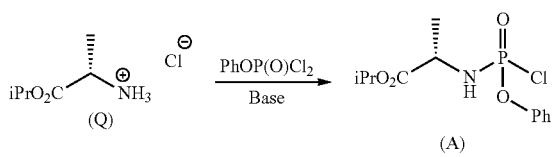

Step g.1), which involves the preparation of the (L)-alanine isopropyl ester hydrochloride (Q) starting from (L)-alanine, can be performed according to one of the techniques known to a man skilled in the art for the preparation of an amino acid isopropyl ester, for example by treatment with a saturated solution of hydrogen chloride in isopropanol.

The next step g.2) involves the conversion of the (L)-alanine isopropyl ester hydrochloride (Q), optionally isolated, into phosphochloride (A) by treatment with phenyl dichlorophosphate in an amount ranging between 0.9 and 1.1 equivalents with respect to the amount of hydrochloride (Q) used, preferably 1 equivalent. Said conversion is carried out in the presence of an organic base, for example a tertiary amine such as triethylamine, N,N-diisopropylethylamine, N,N-diisopropylmethylamine, N-methylmorpholine or N,N-dicyclohexylmethylamine in an ether, for example methyl tert-butyl ether at a temperature normally in the range between −80 and −40° C., preferably between −65 and −55° C. Optionally and preferably, the phosphochloride solution (A) produced in step g.2) is used in the next step a) after removing (for example by filtration) the hydrochloride of the organic base used.

The amount of organic base useful to the purpose is normally between 2 and 3 equivalents with respect to the amount of hydrochloride (Q) used, preferably 2.5 equivalents.

In a second aspect thereof, the present invention relates to a process for the preparation of a diastereomerically purified mixture of nucleoside phosphoramidates (4) comprising the following synthesis steps:

d) preparing a diastereomerically purified form of the phosphoramidate (5):

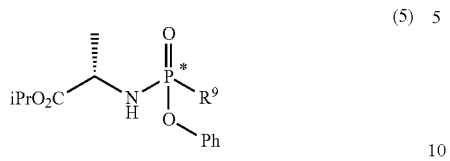

(5)

wherein $R^9$ is an aryloxide substituted with at least one electron-withdrawing group;
e) phosphorylating the nucleoside (6) with the diastereomerically purified form of the phosphoramidate (5) in the presence of an organomagnesium reagent and of an alkaline halide, a zinc halide, a copper halide or a mixture thereof:

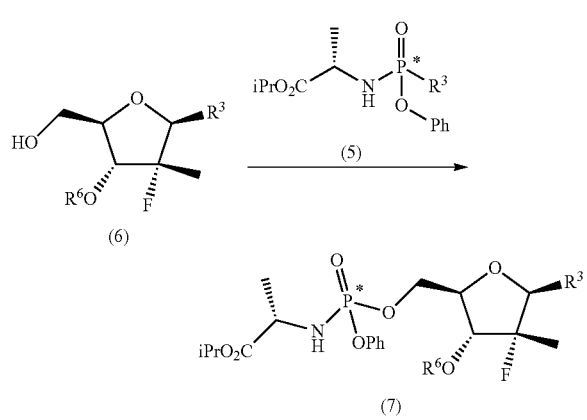

wherein:
$R^3$ can take any of the above meanings; and
$R^6$ is hydrogen or an alcohol protecting group selected from carbonates or ethers;
f) if $R^4$ and $R^6$ are other than hydrogen and $R^3$ is 4-aminouracil or a protected form thereof, converting the compound of general formula (7) into the diastereomerically purified mixture of the nucleoside phosphoramidate (4).

Step d) comprises the preparation of a diastereomerically purified form of phosphoramidate (5) (wherein $R^4$ is an aryloxide substituted with at least one electron-withdrawing group) according to one of the techniques known to the man skilled in the art, for example following the procedure described in the international Aryloxides substituted with at least one electron-withdrawing group useful for the purpose are, for example, selected from 2,4-dinitrophenoxide, 4-nitrophenoxide, 2-nitrophenoxide, 2-chloro-4-nitrophenoxide, 2,4-dichlorophenoxide or preferably pentafluorophenoxide.

Preferably, a diastereomerically purified form of phosphoramidate (5) may be prepared in an operation h) comprising the following synthesis steps:
h.1) preparing the (L)-alanine isopropyl ester hydrochloride (Q);

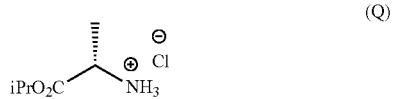

(Q)

h.2) reacting said hydrochloride (Q) with phenyl dichlorophosphate in the presence of a base;

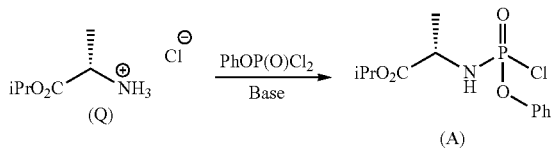

h.3) reacting the phosphochloride (A) with a phenol substituted with at least one electron-withdrawing group ($R^9H$) in the presence of a base to prepare a diastereomerically enriched form of the phosphoramidate (5);

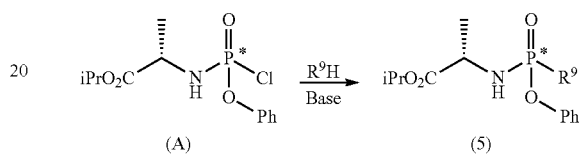

wherein $R^9$ can take any of the above meanings;
h.4) isolating the diastereomerically purified form of phosphoramidate (5) by fractional crystallization.

Step h.1) may for example be performed according to one of the techniques described above to perform step g.1).

The next step h.2) involves the conversion of the (L)-alanine isopropyl ester hydrochloride (Q), optionally isolated, into phosphochloride (A) by treatment with phenyl dichlorophosphate in an amount ranging between 0.9 and 1.1 equivalents with respect to the amount of hydrochloride (Q) used, preferably 1 equivalent and in the presence of a base. Step h.2) is carried out by adding an organic base, for example one of those described above to perform step g. 2) and phenyl dichlorophosphate to a solution of the (L)-alanine isopropyl ester hydrochloride (Q) in an alkylacetate (for example iso-propyl acetate), a chlorinated solvent (for example dichloromethane), an ether or a mixture thereof, cooled to a temperature of between −80 and −40° C., preferably between −65 and −55° C.

The amount of organic base useful to the purpose is normally between 2 and 3 equivalents with respect to the amount of hydrochloride (Q) used, preferably 2.5 equivalents.

Optionally and preferably, the phosphochloride solution (A) produced in step h.2) is used in the next step h.3) without further purification.

Step h.3) involves the conversion of the phosphochloride (A), optionally isolated, into the diastereomerically enriched mixture of phosphoramidate (5) by treatment with a phenol substituted with at least one electron withdrawing group, $R^9H$ (wherein $R^9$ has the meanings given above), in an amount ranging between 0.7 and 1.1 equivalents with respect to the amount of hydrochloride (Q) used in step h.2), preferably of between 0.8 and 1 equivalent. Said conversion is carried out in the presence of an organic base, such as a tertiary amine such as triethylamine, N,N-diisopropylethylamine, N,N-diisopropylmethylamine, N-methylmorpholine or N,N-dicyclohexylmethylamine in an alkylacetate (for example iso-propyl acetate) or a mixture thereof with a chlorinated solvent (preferably dichloromethane) or with an ether, preferably at a temperature of between −25 and 10° C., preferably between −10 and 5° C.

The amount of organic base useful to the purpose is normally between 0.8 and 1.1 equivalents with respect to the amount of hydrochloride (Q) used in step h.2), preferably between 0.9 and 1 equivalent.

The final step h.4) comprises the fractional crystallization of the diastereomerically enriched form of phosphoramidate (5) to obtain the diastereomerically purified form of said phosphoramidate. Crystallization conditions useful for this purpose involve, for example, the use of a solvent mixture comprising an aliphatic hydrocarbon, preferably heptane or hexane, and an alkylacetate, preferably isopropyl or ethyl acetate.

Thereafter, in step e), the diastereomerically purified forms of phosphoramidate (5) optionally solubilized in an ether (preferably tetrahydrofuran) are treated with nucleoside (6) in the presence of an organomagnesium reagent and an alkaline halide (preferably a chloride), such as a lithium, sodium, potassium or cesium chloride, or a zinc or copper halide, to obtain a diastereomerically purified form of the nucleoside phosphoramidate (7). Said phosphorylation reaction takes place at a temperature of between −30 and 20° C., for example between −20 and 0° C., preferably between −10 and −5° C., in an ether, preferably tetrahydrofuran.

Organomagnesium reagents useful for this purpose are, for example, those described above to perform step a) described above.

The amount of phosphoramidate (5) used in the phosphorylation reaction ranges between 1 and 3 equivalents with respect to the amount of nucleoside (6) used, preferably 2 equivalents.

The amount of organomagnesium reagent in the phosphorylation reaction ranges between 1 and 3 equivalents with respect to the amount of nucleoside (6) used, preferably 2 equivalents.

The alkaline or zinc or copper halide is used in an amount ranging between 0.5 and 2 equivalents with respect to the amount of organomagnesium used, preferably 1 equivalent.

The third operation, f), of the process object of the second aspect of the invention can be carried out according to two alternative synthesis schemes, shown below as f.i), f.ii).

The synthesis scheme f.i) can be performed when $R^3$ is uracil, $R^2$ is an alcohol protecting group selected from carbonates or ethers and $R^4$ is hydrogen, or one of the amine protecting groups specified above, and involves the (concurrent or sequential) deprotection of the hydroxyl group in position 3' and/or of the uracil nitrogen, if $R^4$ is other than hydrogen.

This step can be performed according to one of the methods known to the man skilled in the art as described above to perform step b.i) of the process object of the first aspect of the present invention.

The synthesis scheme f.ii) can be performed when $R^3$ is 4-aminouracil, $R^2$ is an alcohol protecting group selected from carbonates or ethers and $R^5$ is hydrogen or one of the amine protecting groups specified above, and involves the deprotection of the hydroxyl group in position 3', the conversion of the 4-aminouracil group in uracil and, if $R^5$ is other than hydrogen, the deprotection of said nitrogen. This step may for example be performed according to one of the methods described above to perform step b.ii).

If $R^3$ is uracil, $R^2$ and $R^4$ are hydrogen, the compound of general formula (7) is a diastereomerically purified mixture of the nucleoside phosphoramidate (4) and therefore, the execution of step f) in the synthesis scheme object of the second aspect of the present invention is optional.

Compounds (2') and (2") are novel and are a further object of the present invention. The nucleosides of general formula (2), with the proviso that $R^2$=benzyl, para-methoxybenzyl, allyl, tetrahydropyranyl (THP), 1-ethoxyethyl, methoxymethyl or para-methoxybenzyloxymethyl, are in turn novel and are a further aspect of the present invention.

The invention will be further described by the following examples.

Example 1

Synthesis of (L)-alanine isopropyl ester hydrochloride

This example is representative of step g.1).

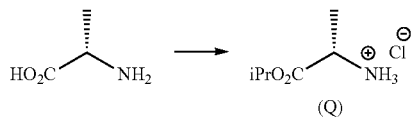

(Q)

To a flask provided with mechanical stirrer, reflux condenser, thermometer and under nitrogen atmosphere are added (L)-alanine (5.0 g, 56.1 mmol) and a solution of hydrogen chloride in isopropanol (11.1% w/w, 73.8 g, 224.5 mmol). The reaction mixture is heated to boiling (80-85° C.) for 4 hours. Once the conversion is complete, controlled in TLC by eluting with 7:3 ethanol-water and developing with ninhydrin, it is concentrated to residue in vacuum removing the iso-propanol co-evaporating the residue multiple times with isopropyl acetate, thus obtaining the desired product (9.4 g quantitative yield) as an oil.

Example 2

Synthesis of (2S)-isopropyl-2-((chloro(phenoxy) phosphoryl)amino)propanoate

This example is representative of step g.2).

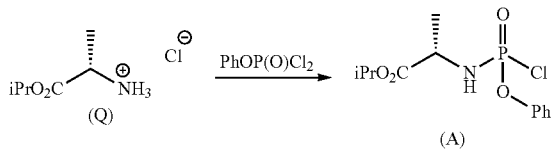

To a flask provided with mechanical stirrer, reflux condenser, thermometer and under nitrogen atmosphere are added (L)-alanine isopropyl ester hydrochloride (9.4 g, 56.1 mmol) and methyl tert-butyl ether (80 mL) and the resulting mixture is stirred at room temperature until a homogeneous suspension is obtained. The mixture is then cooled to between −65° C. and −55° C. by means of a bath of dry ice and acetone and triethylamine (13.0 g, 128.5 mmol) is added, keeping the system at a temperature below −50° C.

At the end of the addition, the mixture is cooled to between −65 and −55° C. and a solution of phenyl dichlorophosphate (10.8 g, 51.2 mmol) in methyl tert-butyl ether (9.5 mL) is added, keeping the temperature below −50° C. The reaction mass is stirred between −65° C. and −55° C. Once the conversion is complete (about two hours), the mass is brought to a temperature of between −25 and −20° C. and filtered under nitrogen atmosphere (to eliminate the triethylamine hydrochloride). The filtrate is stored at −20° C. under nitrogen atmosphere to be used in the next step without further manipulation, given the thermal instability of the desired product. A quantitative yield is considered.

Example 3

Synthesis of (2S)-isopropyl 2-(((((2R,3R,4R,5R)-3-(((benzyloxy)carbonyl)oxy)-5-(2,4-dioxo-3,4-dihydropyrimidin-1(2H)-yl)-4-fluoro-4-methyltetrahydrofuran-2-yl)methoxy)(phenoxy)phosphoryl)amino) propanoate Compound of Formula (3), Wherein R²=Cbz, R³=uracil and R⁴=H This example is representative of step a).

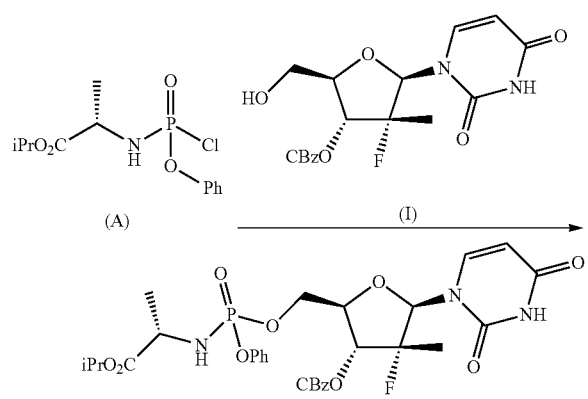

To a flask provided with mechanical stirrer, reflux condenser, thermometer and under nitrogen atmosphere are added benzyl-((2R,3R,4R,5R)-5-(2,4-dioxo-3,4-dihydropyrimidin-1(2H)-yl)-4-fluoro-2-(hydroxymethyl)-4-methyltetrahydrofuran-3-yl) carbonate (I) (10.0 g, 25.4 mmol) and tetrahydrofuran (140 mL). To the solution thus obtained and cooled to between −30 and −25° C. is added iso-propylmagnesium chloride complex 1:1 with lithium chloride (1.3 M in THF, 39 mL, 50.7 mmol), keeping the temperature below −20° C. When the addition is complete, the reaction mixture is stirred between −30 and −20° C. for two hours and a solution of the phosphochloride (A) obtained as described in example 2 (17-18% w/w solution in MTBE, 89 g, 51.2 theoretical mmol) is added over about two hours, keeping the temperature below −20° C. Once the conversion is complete, the reaction mixture is poured, keeping the temperature below 5° C., on a mixture of isopropyl acetate (170 mL.), water (90 mL) and acetic acid (4 mL) cooled to 0-5° C. It is heated to 20-25° C., then the phases are separated, the organic phase is washed with water and concentrated to residue under vacuum, removing the residual solvents by co-evaporation with methanol, keeping the temperature below 40° C. 18.0 g of an amorphous residue are obtained (quantitative yield).

Example 4

Synthesis of (2S)-isopropyl-2-(((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)propanoate Compound of Formula (4)

This example is representative of step b.i).

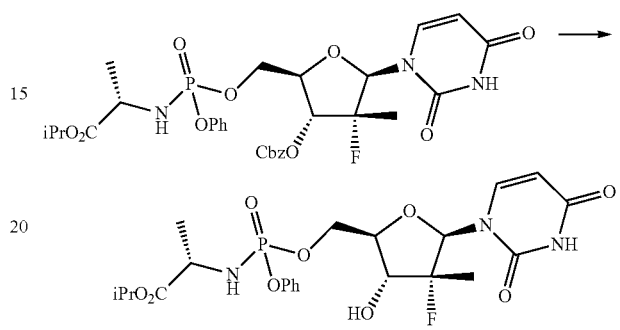

The product obtained in example 3 (18.0 g, 25.4 mmol) dissolved in methanol (130 mL) is hydrogenated at room temperature and pressure using palladium on carbon as a catalyst (10% w/w, 50% wet, 54 mg, 0.025 mmol). Once the conversion is complete (after about 4 hours), the mixture is filtered on a celite pad washing with methanol, then it is concentrated to residue under vacuum. Methanol is removed by repeated co-evaporation with dichloromethane. 14 g of an amorphous residue are obtained (quantitative yield). The HPLC analysis of the residue (conducted as described in *Biomed. Chromatogr.* 2012; 26: 583-588) shows a diastereomeric ratio of Sp:Rp=83:17.

Example 5

Synthesis of Sofosbuvir by Fractional Crystallization of (2S)-isopropyl-2-(((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)propanoate This example is representative of step c).

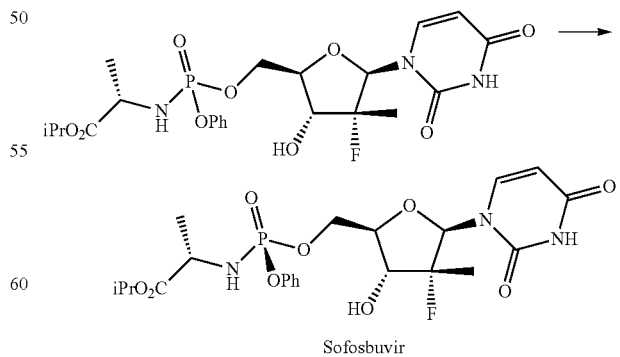

Sofosbuvir

The product obtained as described in example 4 (14 g crude, 25.4 theoretical mmol) is dissolved in dichloromethane (56 mL) at room temperature and n-heptane (14 mL) is added slowly. After precipitation, the mixture is left under stirring for 18 hours, it is cooled to 10° C., left 1 hour at the same temperature, then it is filtered and the resulting solid is washed with dichloromethane. It is dried to 40° C. under vacuum, giving 8.7 g of a product with a diastereomeric ratio of Sp:Rp=96:4 (65% yield starting from the phosphorylation step of compound (I)). The solid thus obtained is crystallized again from a mixture of dichloromethane (36 mL) and acetonitrile (9 mL), dissolving it under reflux and then cooling to 0° C. over about 2 hours. It is filtered, washed with dichloromethane and dried to 40° C. under vacuum, giving 7.8 g (90% yield) of product with a diastereomeric ratio of Sp:Rp=99.9:0.1.

Example 6 (Comparative)

Synthesis of (2S)-isopropyl-2-(((((2R,3R,4R,5R)-3-(((benzyloxy)carbonyl)oxy)-5-(2,4-dioxo-3,4-dihydropyrimidin-1(2H)-yl)-4-fluoro-4-methyltetrahydrofuran-2-yl)methoxy)(phenoxy)phosphoryl)amino) propanoate Compound of Formula (3), Wherein R²=Cbz, R³=uracil and R⁴=H This example is representative of step a).

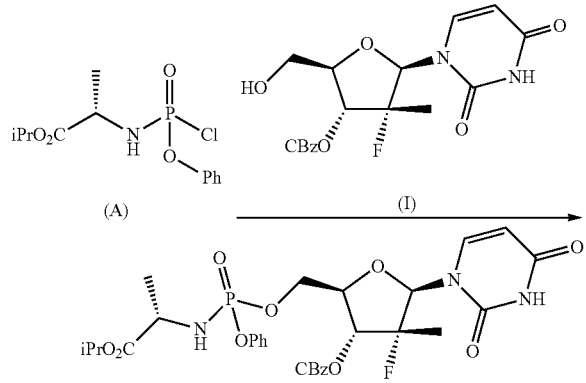

To a flask provided with mechanical stirrer, reflux condenser, thermometer and under nitrogen atmosphere are added benzyl-((2R,3R,4R,5R)-5-(2,4-dioxo-3,4-dihydropyrimidin-1(2H)-yl)-4-fluoro-2-(hydroxymethyl)-4-methyltetrahydrofuran-3-yl) carbonate (1) prepared as described in example 3 (10.0 g, 25.4 mmol) and tetrahydrofuran (140 mL). To the solution thus obtained and cooled to between −30 and −25° C. is added tert-buty/magnesium chloride (1.0 M in THF, 51 mL, 50.7 mmol), keeping the temperature below −20° C. When the addition is complete, the reaction mixture is stirred between −30 and −20° C. for two hours and a solution of the phosphochloride (A) obtained as described in example 2 (17-18% w/w solution in MTBE, 90 g, 51.2 theoretical mmol) is added over about two hours, keeping the temperature below −20° C. Once the conversion is complete, the reaction mixture is poured, keeping the temperature below 5° C., on a mixture of isopropyl acetate (170 mL), water (90 mL) and acetic acid (4 mL) cooled to 0-5° C. It is heated to 20-25° C., then the phases are separated, the organic phase is washed with water and concentrated to residue under vacuum, removing the residual solvents by co-evaporation with methanol, keeping the temperature below 40° C. 18.2 g of an amorphous residue are obtained (quantitative yield). An exact determination of the diastereomeric ratio via HPLC is carried out after removing the Cbz group as described in example 4. The resulting product shows a diastereomeric ratio of Sp:Rp=65:35.

Example 7

Synthesis of (2S)-isopropyl-2-(((perfluorophenoxy)(phenoxy)phosphoryl)amino)propanoate

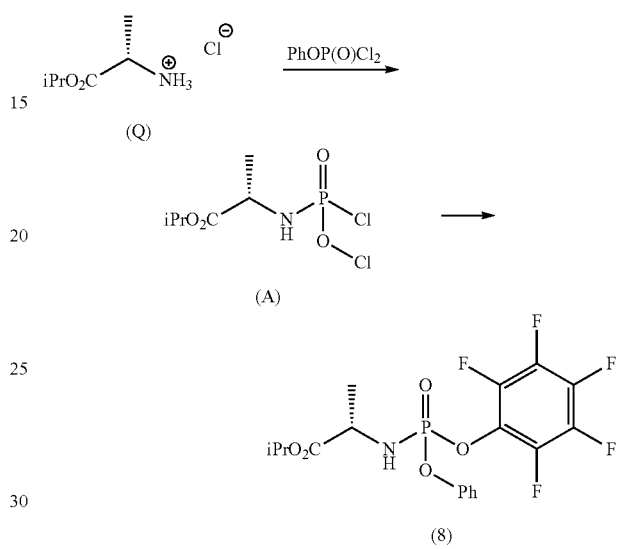

To a flask provided with mechanical stirrer, reflux condenser, thermometer and under nitrogen atmosphere is added a solution of (L)-alanine isopropyl ester hydrochloride (Q) (2.8 g, 16.8 mmol) obtained as described in example 1 and dichloromethane (21 mL). The resulting mixture is stirred at room temperature until obtaining a homogeneous suspension. The mixture is then cooled to between −65° C. and −55° C. by means of a bath of dry ice and acetone and triethylamine (3.9 g, 38.8 mmol) is added, keeping the temperature below −50° C.

At the end of the addition, the mixture is cooled to between −65 and −55° C. and a solution of phenyl dichlorophosphate (3.3 g, 15.6 mmol) in dichloromethane (11 mL) is added, keeping the temperature below −50° C. The reaction mass is stirred between −65 and −55° C. up to complete conversion (about 1 hour). To a second flask provided with mechanical stirrer, reflux condenser, thermometer and under nitrogen atmosphere are added pentafluorophenol (2.4 g, 13.0 mmol) and dichloromethane (28 mL). The mixture is then cooled to between 0 and 5° C. and triethylamine (1.6 g, 15.8 mmol) is added, keeping the temperature below 10° C. At the end of the addition, the mixture is brought to 20-25° C. and kept under the same conditions for 1 hour, then added to the mixture prepared in the first flask, cooled to a temperature of between −15 and −10° C., keeping the internal temperature below 5° C. At the end of the addition, the resulting reaction mixture is brought to 0-5° C. and kept under the same conditions until the conversion is complete (about 1 hour). Water is added (8.7 mL) to the mass, keeping the temperature below 10° C. It is heated to 20-25° C., then the phases are separated, the organic phase is washed with water and is concentrated under vacuum to residue, removing the residual solvents by co-evaporation with iso-propyl acetate. 9.0 g of residue are obtained (quantitative yield) with a diastereomeric ratio of Sp:Rp=50:50.

Example 8

Synthesis of the Diastereomerically Purified Form of (S)-isopropyl-2-((S)-(perfluorophenoxy)(phenoxy)phosphorylamino)propanoate by Fractional Crystallization

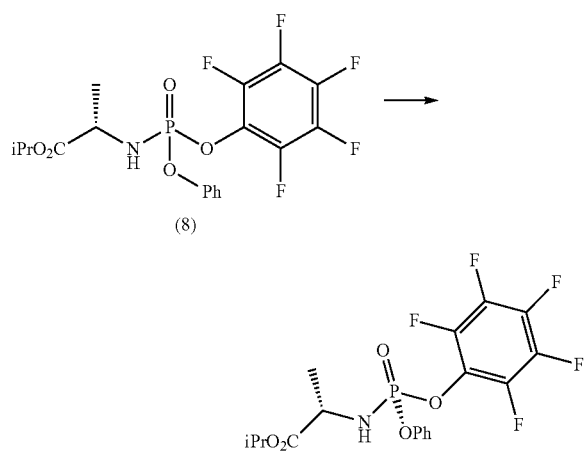

To the product obtained in example 7 (9.0 g crude, 13.0 theoretical mmol) are added iso-propyl acetate (10 mL) and n-heptane (27 mL) and it is heated to a temperature of between 55 and 60° C. until complete dissolution. The resulting solution is slowly cooled to 0-5° C. and left in the same condition until precipitation is complete (about 2 hours). The resulting solid is filtered and washed with a mixture of iso-propyl acetate and n-heptane 1:2 (v/v). It is dried to 40° C. under vacuum, giving 1.5 g of a product with a diastereomeric ratio of Sp:Rp=99.9:0.1 (25% yield starting from the phosphochloride (A)) determined by the HPLC method described on page 107 of the international application WO 2011/123645 A2.

Example 9

Synthesis of Sofosbuvir

This example is representative of step e)

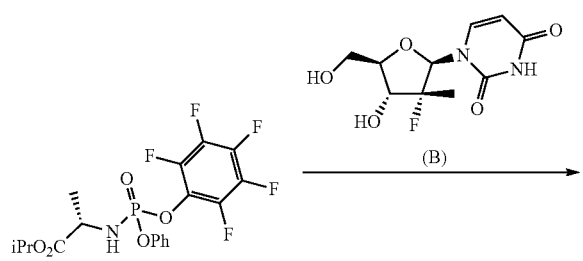

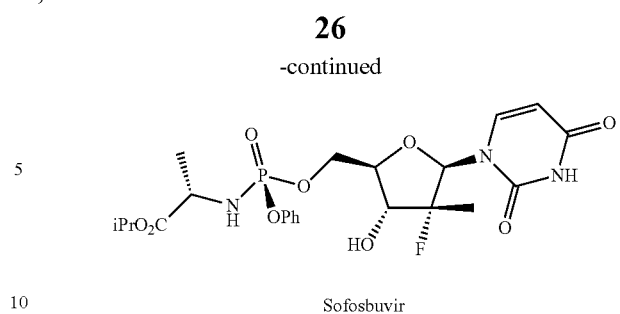

Sofosbuvir

To a flask provided with mechanical stirrer, reflux condenser, thermometer and under nitrogen atmosphere is added 1-((2R,3R,4R,5R)-3-fluoro-4-hydroxy-5-(hydroxymethyl)-3-methyltetrahydrofuran-2-il)pyrimidin-2,4(1H,3H)-dione (B) (10.0 g, 38.4 mmol) and tetrahydrofuran (140 mL). To the solution thus obtained and cooled to between −10 and −5° C. is added iso-propylmagnesium chloride complex 1:1 with lithium chloride (1.3 M in THF, 65 mL, 84.5 mmol), keeping the temperature below −5° C. When the addition is complete the reaction mixture is stirred between 0 and 5° C. for 2 hours and a solution of the product of example 8 (23.5 g, 51.9 mmol) in tetrahydrofuran (106 mL) is added over about 1 hour keeping the temperature below −5° C. Once the conversion is complete (after about 24 hours), the reaction mixture is poured, keeping the temperature below 10° C., on a mixture of iso-propyl acetate (120 mL), water (50 mL) and acetic acid (5 mL) cooled to 0-5° C. it is heated to 20-25° C., then the phases are separated, the organic phase is concentrated under vacuum to residue, then iso-propyl acetate (120 mL) is added and the organic phase is washed with a 5% sodium carbonate solution and with water. The organic phase is concentrated to residue moving the residual solvents by co-evaporation with dichloromethane. The analysis of the three HPLC main peaks shows the following composition: 1.1% (B), 3.83% (Diphosphorylate) and 95.1% Sofosbuvir:

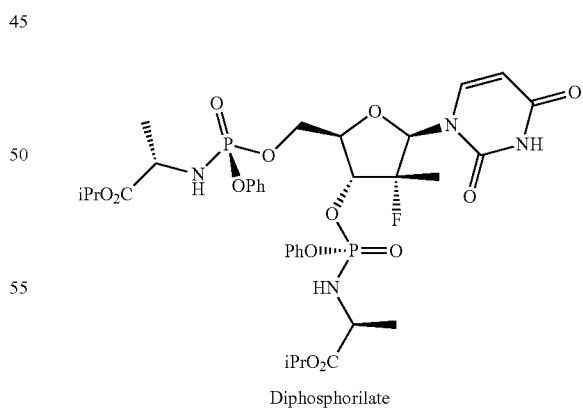

Diphosphorilate

The residue is crystallized by dichloromethane. It is filtered, washed with dichloromethane and dried to 40° C. under vacuum, giving 10.8 g (53% yield) of product with a diastereomeric ratio of Sp:Rp=99.9:0.1.

Example 10

Synthesis of (2S)-isopropyl 2-(((perfluorophenoxy)(phenoxy)phosphoryl)amino)propanoate This example is representative of steps h.2) e h.3)

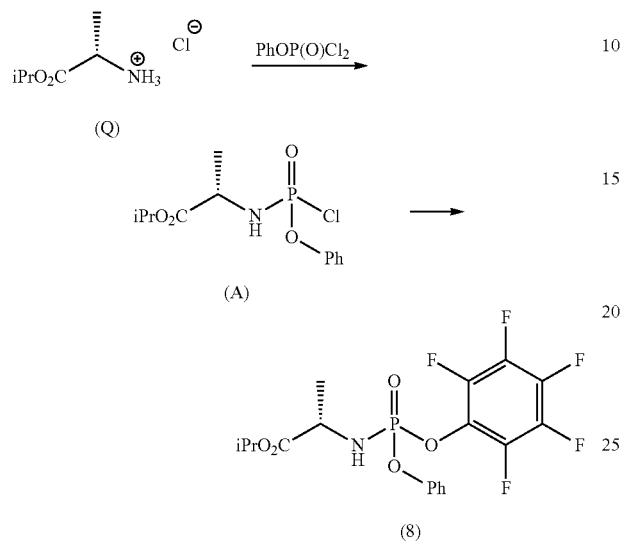

To a flask provided with mechanical stirrer, reflux condenser, thermometer and under nitrogen atmosphere is added a solution of (L)-alanine isopropyl ester hydrochloride (Q) (2.8 g, 16.8 mmol) obtained as described in example 1 and iso-propyl acetate (21 mL). The resulting mixture is stirred at room temperature until a homogeneous suspension is obtained. The mixture is then cooled to between −65° C. and −55° C. by means of a bath of dry ice and acetone and triethylamine (3.9 g, 38.8 mmol) is added, keeping the temperature below −50° C.

At the end of the addition, the mixture is cooled to between −65 and −55° C. and a solution of phenyl dichlorophosphate (3.3 g, 15.6 mmol) in dichloromethane (11 mL) is added, keeping the temperature below −50° C. The reaction mass is stirred between −65 e −55° C. until the conversion is complete (about 1 hour). To a second flask provided with mechanical stirrer, reflux condenser, thermometer and under nitrogen atmosphere, are added pentafluorophenol (2.4 g, 13.0 mmol) and dichloromethane (28 mL). The mixture is then cooled to between 0 and 5° C. and triethylamine (1.6 g, 15.8 mmol) is added, keeping the temperature below 10° C. At the end of the addition, the mixture is brought to 20-25° C. and kept under the same conditions for 1 hour, then added to the mixture prepared in the first flask, cooled to a temperature of between −15 and −10° C., keeping the internal temperature below 5° C. At the end of the addition, the resulting reaction mixture is brought to 0-5° C. and kept under the same conditions until the conversion is complete (about 1 hour). Water is added (8.7 mL) to the mass, keeping the temperature below 10° C. It is heated to 20-25° C., then the phases are separated, the organic phase is washed with water and concentrated under vacuum to residue, moving the residual solvents by co-evaporation with iso-propyl acetate. 9.0 g of residue (quantitative yield) are obtained of a product with a diastereomeric ratio of Sp:Rp=64:36.

Example 11

Preparation of Form Diastereomerically Purified of (S)-isopropyl-2-(((S)-(perfluorophenoxy)(phenoxy)phosphoryl)amino)propanoate by Fractional Crystallization This example is representative of step h.4)

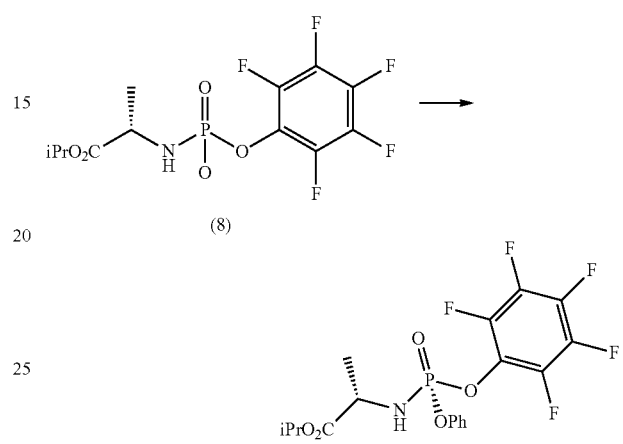

To the product obtained in example 10 (9.0 g crude, 13.0 theoretical mmol) are added iso-propyl acetate (10 mL) and n-heptane (27 mL) and it is heated to a temperature of between 55 and 60° C. until complete dissolution. The resulting mixture is slowly cooled to 0-5° C. and left in the same condition until precipitation is complete (about 2 hours). The resulting solid is filtered and washed with a mixture of iso-propyl acetate and n-heptane 1:2 (v/v). It is dried to 40° C. under vacuum, giving 1.5 g of a product with a diastereomeric ratio of Sp:Rp=99.9:0.1 (33% yield starting from the phosphochloride (A)) determined by the HPLC method described on page 107 of the international application WO 2011/123645 A2.

Example 12

Synthesis of (2S)-isopropyl-2-(((((2R,3R,4R,5R)-3-(((benzyloxy)carbonyl)oxy)-5-(2,4-dioxo-3,4-dihydropyrimidin-1(2H)-yl)-4-fluoro-4-methyltetrahydrofuran-2-yl)methoxy)(phenoxy)phosphoryl)amino)propanoate Compound of Formula (3), wherein $R^2$=Cbz, $R^3$=uracil and $R^4$=H This example is representative of step a)

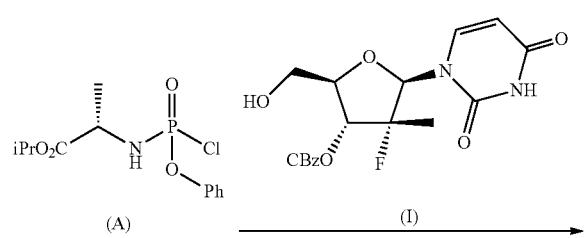

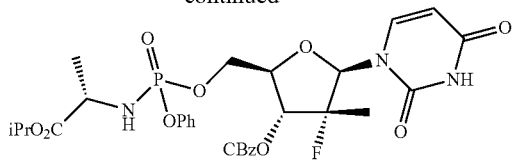

To a flask provided with mechanical stirrer, reflux condenser, thermometer and under nitrogen atmosphere are added benzyl ((2R,3R,4R,5R)-5-(2,4-dioxo-3,4-dihydropyrimidin-1(2H)-yl)-4-fluoro-2-(hydroxymethyl)-4-methyltetrahydrofuran-3-yl) carbonate (1) prepared as described in example 3 (4.6 g, 11.7 mmol) and tetrahydrofuran (65 mL). To the solution thus obtained and cooled to between −30 and −25° C. are added tert-butylmagnesium chloride (1.0 M in THF, 23.4 mL, 23.4 mmol) and LiCl (990 mg, 23.4 mmol). When the addition is complete the reaction mixture is stirred between −30 and −20° C. for two hours and a solution of the phosphochloride (A) obtained as described in example 2 (17-18% w/w solution in MTBE, 7.2 g, 23.4 mmol) is added over about two hours, keeping the temperature below −20° C. Once the conversion is complete, the reaction mixture is poured, keeping the temperature below 5° C., on a mixture of iso-propyl acetate (80 mL), water (40 mL) and acetic acid (2 mL) cooled to 0-5° C. It is heated to 20-25° C., then the phases are separated, the organic phase is washed with water and concentrated under vacuum to residue, moving the residual solvents by co-evaporation with methanol keeping the temperature below 40° C. 8.2 g of an amorphous residue are obtained (quantitative yield). An exact determination of the diastereomeric ratio via HPLC is carried out after removing the Cbz group as described in example 4. The resulting product (6.8 g quantitative yield) shows a diastereomeric ratio of Sp:Rp=69:31.

Example 13 (Comparative)

Synthesis of (2S)-isopropyl-2-((((2R,3R,4R,5R)-3-(((benzyloxy)carbonyl)oxy)-5-(2,4-dioxo-3,4-dihydropyrimidin-1(2H)-yl)-4-fluoro-4-methyltetrahydrofuran-2-yl)methoxy)(phenoxy)phosphoryl)amino) propanoate Compound of Formula (3), Wherein $R^2$=Cbz, $R^3$=uracil and $R^4$=H This example is representative of step a)

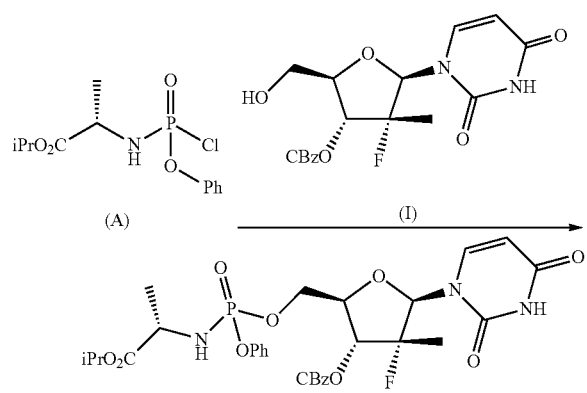

To a flask provided with mechanical stirrer, reflux condenser, thermometer and under nitrogen atmosphere are added benzyl-((2R,3R,4R,5R)-5-(2,4-dioxo-3,4-dihydropyrimidin-1(2H)-yl)-4-fluoro-2-(hydroxymethyl)-4-methyltetrahydrofuran-3-yl) carbonate (I) prepared as described in example 3 (4.6 g, 11.7 mmol) and tetrahydrofuran (72 mL). To the solution thus obtained and cooled to between −30 and −25° C. is added iso-propylmagnesium chloride (2.0 M in THF, 11.7 mL, 23.4 mmol), keeping the temperature below −20° C. When the addition is complete the reaction mixture is stirred between −30 and −20° C. for two hours and a solution of the phosphochloride (A) obtained as described in example 2 (17-18% w/w solution in MTBE, 7.2 g, 23.4 mmol) is added over about two hours, keeping the temperature below −20° C. Once the conversion is complete, the reaction mixture is poured, keeping the temperature below 5° C., on a mixture of iso-propyl acetate (80 mL), water (4 mL) and acetic acid (2 mL) cooled to 0-5° C. It is heated to 20-25° C., then the phases are separated, the organic phase is washed with water and concentrated under vacuum to residue, moving the residual solvents by co-evaporation with methanol keeping the temperature below 40° C. 8.0 g of an amorphous residue are obtained (quantitative yield). An exact determination of the diastereomeric ratio via HPLC is carried out after removing the Cbz group as described in example 4. The resulting product (6.5 g quantitative yield) shows a diastereomeric ratio of Sp:Rp=66:34.

Example 14

Synthesis of 3-benzyl-1-((2R,3R,4R,5R)-4-(benzyloxy)-5-((tert-butyldimethylsilyloxy)methyl)-3-fluoro-3-methyltetrahydrofuran-2-yl)pyrimidin-2,4 (1H,3H)-dione Compound of Formula (11), Wherein $R^7$ is tert-butyldimethylsilyl and $R^{10}$ and $R^{11}$ are benzyl This example is representative of step j.ii.2)

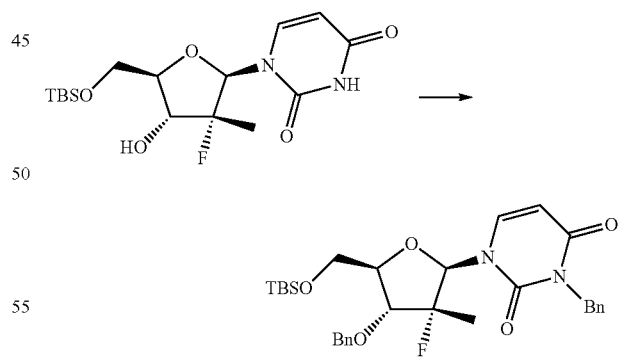

To a flask provided with mechanical stirrer, reflux condenser, thermometer and under nitrogen atmosphere are added 1-((2R,3R,4R,5R)-5-(((tert-butyldimethylsilyl)oxy) methyl)-3-fluoro-4-hydroxy-3-methyltetrahydrofuran-2-yl) pyrimidin-2,4(1H,3H)-dione prepared as described in Tetrahedron (2011), 67, 5487-5493 (500 mg, 1.3 mmol) and dimethylformamide (3 mL). To the solution thus obtained and cooled to 0° C. is added 60% NaH in mineral oil (110 mg, 2.7 mmol), keeping the temperature between 0 and 5°

C., and benzyl bromide (320 μL, 2.7 mmol) drop-wise after ten minutes. When the addition is complete, temperature is raised to 25° C. and it is kept under stirring until the conversion is complete, monitored by petroleum ether TLC/EtOAc 7:3 (about 16 hours). The reaction mixture, cooled to 0° C., is diluted with diethyl ether. Phases are separated and the aqueous phase is extracted with diethyl ether; the organic phases are combined and dried over anhydrous sodium sulphate, filtered and concentrated to residue under vacuum.

The product is purified by chromatographic column (eluent petroleum ether/EtOAc 7:3) as colourless oil (811 mg, 86%).

$^1$H NMR (400 MHz, CDCl$_3$) δ 7.87 (d, J=8.0 Hz, 1H), 7.48-7.14 (m, 10H), 6.19 (d, J=17.9 Hz, 1H), 5.73 (d, J=8.0 Hz, 1H), 5.15-5.02 (m, 2H), 4.74-4.59 (m, 2H), 4.15-4.10 (m, 2H), 3.92-3.78 (m, 2H), 1.23 (d, J=24.0 Hz, 3H), 0.93 (s, 9H), 0.11 (s, 6H).

MS (ES): 555 (M+H)$^+$, 567 (M+Na)$^+$.

Example 15

Synthesis of 3-benzyl-1-((2R,3R,4R,5R)-4-benzyloxy)-3-fluoro-5-(hydroxymethyl)-3-methyltetrahydrofuran-2-yl)pyrimidin-2,4(1H,3H)-dione Compound of Formula (2″), Wherein R$^{10}$ and R$^{11}$ are benzyl This example is representative of step j.ii.3)

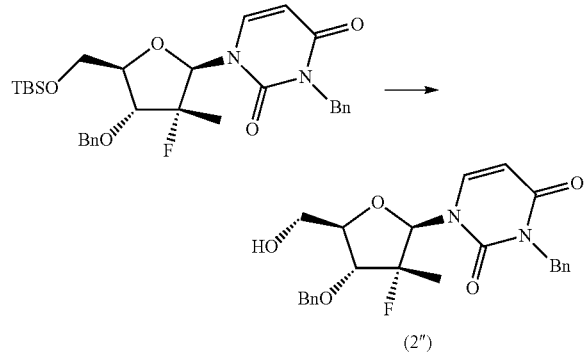

(2″)

To a flask provided with mechanical stirrer, reflux condenser, thermometer and under nitrogen atmosphere are loaded 3-benzyl-1-((2R,3R,4R,5R)-4-(benzyloxy)-5-((tert-butyldimethylsiloxy)methyl)-3-fluoro-3-methyltetrahydrofuran-2-yl)pyrimidin-2,4(1H,3H)-dione prepared as described in example 14 (2.5 g, 4.5 mmol) and tetrahydrofuran (50 mL). To the solution thus obtained tetrabutylammonium fluoride (2.1 g, 6.8 mmol) is added while keeping the mixture under stirring until the conversion is complete (about 1 hour). The product is concentrated to residue and purified by chromatographic column (eluent EtOAc) as a white solid (1.2 g, 62%).

$^1$H NMR (400 MHz, CDCl$_3$) δ 7.77 (s, 1H), 7.48-7.12 (m, 10H), 6.02 (d, J=16.0 Hz, 1H), 5.71 (d, J=8.0 Hz, 1H), 5.13-5.01 (m, 2H), 4.75-4.59 (nm, 2H), 4.10-4.02 (m, 3H), 3.71 (d, J=12.0 Hz, 1H), 2.55 (s, 1H), 1.23 (d, J=24.0 Hz, 3H).

MS (ES): 441 (M+H)$^+$, 463 (M+Na)$^+$.

Example 16

Synthesis of isopropyil ((((2R,3R,4R,5R)-5-(3-benzyl-2,4-dioxo-3,4-dihydropyrimidin-1(2H)-yl)-3-(benzyloxy)-4-fluoro-4-methy/tetrahydrofuran-2-yl)methoxy)(phenoxy)phosphoryl)-L-alaninate Compound of Formula (3), Wherein R$^2$=benzyl, R$^3$=uracil and R$^4$=benzyl This example is representative of step a)

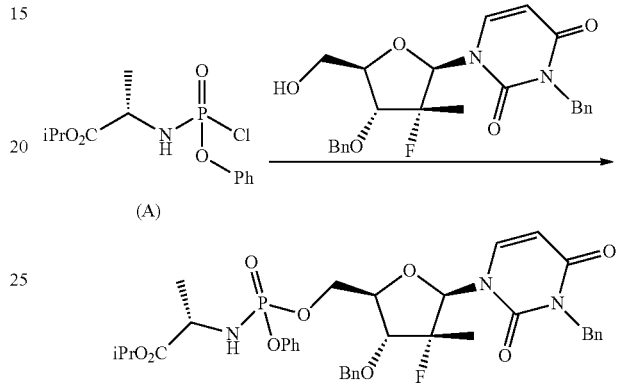

To a flask provided with mechanical stirrer, reflux condenser, thermometer and under nitrogen atmosphere are added 3-benzyl-1-((2R,3R,4R,5R)-4-(benzyloxy)-3-fluoro-5-(hydroxymethyl)-3-methyltetrahydrofuran-2-yl)pyrimidin-2,4(1H,3H)-dione (10.0 g, 25.4 mmol) and tetrahydrofuran (140 mL). To the solution thus obtained and cooled to between −15 and −10° C. is added iso-propylmagnesium chloride complex 1:1 with lithium chloride (1.3 M in THF, 39 mL, 50.8 mmol), keeping the temperature below −5° C. When the addition is complete the reaction mixture is stirred between −20 and −10° C. for two hours and a solution of the phosphochloride (A) obtained as described in example 2 (17-18% w/w solution in MTBE, 120 g, 68.6 theoretical mmol) is added over about two hours, keeping the temperature below −10° C. Once the conversion is complete, the reaction mixture is poured, keeping the temperature below 5° C., on a mixture of isopropyl acetate (170 mL), water (90 mL) and acetic acid (4 mL) cooled to 0-5° C. It is heated to 20-25° C., then the phases are separated, the organic phase is washed with water and concentrated under vacuum to residue, moving the residual solvents by co-evaporation with methanol keeping the temperature below 40° C. 19.2 g of residue are obtained (quantitative yield).

HPLC analysis of the crude product (carried out by means of a Symmetry® C18 column (4.6 mm×25 mm, 5 μm) as eluent H$_2$O (+0.1% H$_3$PO$_3$)CH$_3$CN 45:55 at 1 mL/min and UV 254 nm detector) shows a 97% conversion and a diastereomeric ratio of Sp:Rp=93:7.

$^1$H NMR (400 MHz, CDCl$_3$) δ 7.54-6.91 (m, 16H), 6.14 (d, J=18.6 Hz, 1H), 5.69 (m, J=8.0 Hz, 1H), 5.12-4.93 (m, 3H), 4.80-4.59 (m, 2H), 4.59-4.47 (m, 1H), 4.59-4.47 (m, 1H), 4.28 (dd, J=11.5, 6.8 Hz, 1H), 4.25-4.01 (m, 1H), 3.93-3.37 (m, 2H), 1.38-1.15 (m, 12H).

MS (ES): 732 (M+Na)$^+$.

Example 17

Synthesis of 1-((2R,3R,4R,5R)-4-(benzyloxy)-5-(((tert-butyldimethylsilyl)oxy)methyl)-3-fluoro-3-methyltetrahydrofuran-2-yl)pyrimidin-2,4(1H,3H)-dione Compound of Formula (10), Wherein R⁷ is tert-butyldimethylsilyl and R¹⁰ is benzyl This example is representative of step j.i.2)

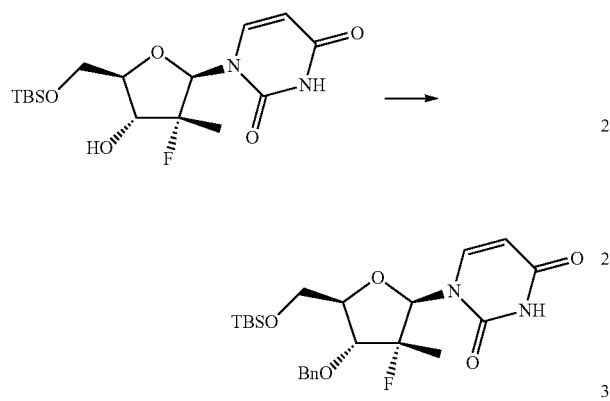

To a flask provided with mechanical stirrer, reflux condenser, thermometer and under nitrogen atmosphere are added 1-((2R,3R,4R,5R)-5-(((tert-butyldimethylsilyl)oxy)methyl)-3-fluoro-4-hydroxy-3-methyltetrahydrofuran-2-yl)pyrimidin-2,4-(1H,3H)-dione prepared as described in *Tetrahedron* (2011). 67, 5487-5493 (1.8 g, 4.9 mmol) and tetrahydrofuran (20 mL). To the solution thus obtained and cooled to −10° C. is added 60% NaH in mineral oil (593 mg, 14.8 mmol), in subsequent portions and waiting for the effervescence to cease between an addition and the next one. The mixture is maintained at a temperature between −15 and −10° C. for 30 minutes, then benzyl bromide (588 µL, 4.9 mmol) is added drop-wise. When the addition is complete, temperature is raised to 25° C. and it is kept under stirring until the conversion is complete, monitored by TLC petroleum ether/EtOAc 7:3 (about 12 hours). The reaction mixture, cooled to 0° C., is diluted with ethyl acetate. Phases are separated and the aqueous phase is extracted with ethyl acetate; the organic phases are combined and dried over sodium sulphate, filtered and concentrated to residue under vacuum.

The product is purified by chromatographic column (using a gradient from petroleum ether alone to EtOAc alone) as colourless oil (360 mg, 58%).

$^1$H NMR (400 MHz, CDCl$_3$) δ 9.73 (s, 1H), 7.91 (d, J=5.6 Hz, 1H), 7.45-7.21 (m, 5H), 6.17 (d, J=17.8 Hz, 1H), 5.68 (d, J=8.1 Hz, 1H), 4.76-4.61 (m, 2H), 4.16-4.65 (m, 2H), 3.98-3.78 (m, 2H), 1.24 (d, J=24.0 Hz, 3H), 0.93 (s, 9H), 0.10 (s, 6H).

MS (ES): 487 (M+Na)⁺.

Example 18

Synthesis of 1-((2R,3R,4R,5R)-4-(benzyloxy)-3-fluoro-5-(hydroxymethyl)-3-methyltetrahydrofuran-2-yl)pyrimidin-2,4(1H,3H)-dione Compound of Formula (2') Wherein R¹⁰ is benzyl This example is representative of step j.i.3)

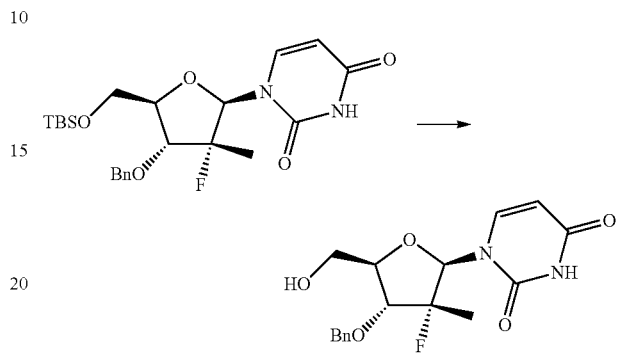

To a flask provided with mechanical stirrer, reflux condenser, thermometer and under nitrogen atmosphere are loaded 1-((2R,3R,4R,5R)-4-(benzyloxy)-5-(((tert-butyldimethylsilyl)oxy)methyl)-3-fluoro-3-methyltetrahydrofuran-2-yl)pyrimidin-2,4(1H,3H)-dione prepared as described in example 17 (1.3 g, 2.8 mmol) and tetrahydrofuran (25 mL). To the solution thus obtained tetrabutylammonium fluoride (1.3 g, 4.2 mmol) is added while keeping the mixture under stirring until the conversion is complete (about 1 hour). The product is concentrated to residue and purified by chromatographic column (eluent EtOAc) as a white solid (617 mg, 63%).

Alternatively, the product may by purified by crystallization by dichloromethane or a mixture of ethyl acetate and methanol.

$^1$H NMR (400 MHz, CDCl$_3$) δ 8.49 (s, 1H), 7.73 (d, J=8.1 Hz, 1H), 7.47-7.28 (m, 5H), 6.04 (d, J=18.7 Hz, 1H), 5.70 (dd, J=8.1, 1.8 Hz, 1H), 4.78-4.66 (m, 2H), 4.18-3.86 (m, 3H), 3.81-3.55 (m, 1H), 1.58 (s, 1H), 1.33 (d, J=22.0 Hz, 3H).

MS (ES): 373 (M+Na)⁺.

Example 19

Synthesis of isopropyl ((((2R,3R,4R,5R)-3-(benzyloxy)-5-(2,4-dioxo-3,4-dihydropyrimidin-1(2H)-yl)-4-fluoro-4-methyltetrahydrofuran-2-yl)methoxy)(phenoxy)phosphoryl)-L-alaninate Compound of Formula (3), Wherein R²=benzyl, R³=uracil and R⁴=hydrogen This example is representative of step a)

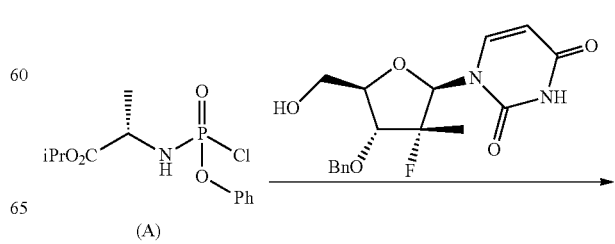

(A)

-continued

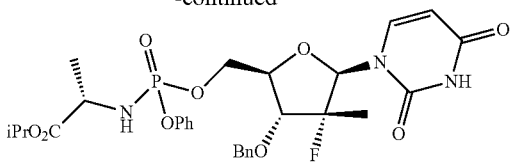

To a flask provided with mechanical stirrer, reflux condenser, thermometer and under nitrogen atmosphere are loaded 1-((2R,3R,4R,5R)-4-(benzyloxy)-3-fluoro-5-(hydroxymethyl)-3-methyltetrahydrofuran-2-yl)pyrimidin-2,4(1H,3H)-dione (10.0 g, 25.4 mmol) and tetrahydrofuran (140 mL). To the solution thus obtained and cooled to between −15 and −10° C. is added iso-propylmagnesium chloride complex 1:1 with lithium chloride (1.3 M in THF, 59 mL, 76.7 mmol), keeping the temperature below −5° C. When the addition is complete the reaction mixture is stirred between −20 and −10° C. for two hours and a solution of the phosphochloride (A) obtained as described in example 2 (17-18% w/w solution in MTBE, 120 g, 68.6 theoretical mmol) is added over about two hours, keeping the temperature below −10° C. Once the conversion is complete, the reaction mixture is poured, keeping the temperature below 5° C., on a mixture of isopropyl acetate (170 mL), water (90 mL) and acetic acid (4 mL) cooled to 0-5° C. It is heated to 20-25° C., then the phases are separated, the organic phase is washed with water and concentrated under vacuum to residue, moving the residual solvents by co-evaporation with methanol keeping the temperature below 40° C. 16.9 g of residue are obtained (quantitative yield).

HPLC analysis of the crude product (carried out by means of a Symmetry® C18 column (4.6 mm×25 mm, 5 μm) as eluent H₂O (+0.1% H₃PO₃)/CH₃CN 45:55 at 1 mL/min and UV 254 nm detector) shows a 98% conversion and a diastereomeric ratio of Sp:Rp=92:8.

Example 20

Synthesis of Sofosbuvir

This example is representative of step b.i)

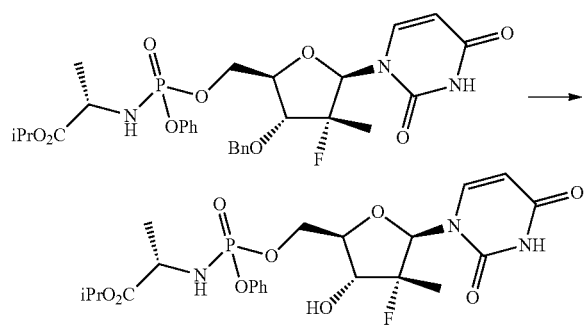

The product obtained in example 19 (16.9 g, 25.4 theoretical mmol) dissolved in methanol (200 mL) is hydrogenated at room pressure and temperature using palladium on carbon as a catalyst (10% w/w, 50% wet, 2.7 g, 1.3 mmol). Once the conversion is complete (after about 12 hours), the mixture is filtered on a celite pad washing with methanol, then it is concentrated to residue under vacuum. Methanol is removed by repeated co-evaporation with dichloromethane. 14.1 g of residue are obtained (quantitative yield). HPLC analysis of the residue (carried out by means of a Symmetry® C18 column (4.6 mm×25 mm, 5 μm) as eluent H₂O (+0.1% H₃PO₃)/CH₃CN 45:55 at 1 mL/min and UV 254 nm detector) shows a quantitative conversion and a diastereomeric ratio of Sp:Rp=92:8.

Example 21

Synthesis of 1-((2R,3R,4R,5R)-4-(allyloxy)-5-((((tert-butyldimethylsilyl)oxy)methyl)-3-fluoro-3-methyltetrahydrofuran-2-yl)pyrimidin-2,4(1H,3H)-dione Compound of Formula (10), Wherein $R^7$ is tert-butyldimethylsilyl and $R^{10}$ is allyl This example is representative of step j.i.2)

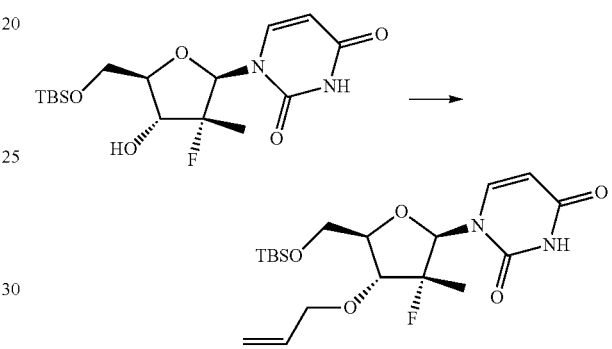

To a flask provided with mechanical stirrer, reflux condenser, thermometer and under nitrogen atmosphere are loaded 1-((2R,3R,4R,5R)-5-((((tert-buthyldimethylsilyl)oxy)methyl)-3-fluoro-4-hydroxy-3-methyltetrahydrofuran-2-yl)pyrimidin-2,4-(1H,3H)-dione prepared as described in *Tetrahedron* (2011), 67, 5487-5493 (1.6 g, 4.2 mmol) and tetrahydrofuran (18 mL). To the solution thus obtained and cooled to −10° C. is added 60% NaH in mineral oil (504 mg, 12.6 mmol), in subsequent portions and waiting for the effervescence to cease between an addition and the next one. The mixture is maintained at a temperature between −15 and −10° C. for 30 minutes, then allyl bromide (370 μL, 4.2 mmol) is added drop-wise. When the addition is complete, temperature is left to raise to 25° C. and it is kept under stirring until the conversion is complete, monitored by TLC petroleum ether/EtOAc 7:3 (about 12 hours). The reaction mixture, cooled to 0° C., is diluted with ethyl acetate. Phases are separated and the aqueous phase is extracted with ethyl acetate; the organic phases are combined and dried over sodium sulphate, filtered and concentrated to residue under vacuum.

The product is purified by chromatographic column (using a gradient from petroleum ether alone to EtOAc alone) bringing to 1.3 g of the desired product (yield: 74%).

¹H NMR (400 MHz, CDCl₃) δ 9.96 (s, 1H), 7.91 (d, J=4.4 Hz, 1H), 6.14 (d, J=17.6 Hz, 1H), 5.90-5.80 (m, 1H), 5.66 (d, J=8.0 Hz, 1H), 5.27-5.18 (m, 2H), 4.14-4.05 (m, 4H), 3.82-4.80 (m, 2H), 1.38 (d, J=22.0 Hz, 3H), 0.89 (s, 9H), 0.09 (s, 3H), 0.08 (s, 3H).

MS (ES): 415 (M+H)⁺, 437 (M+Na)⁺.

Example 22

Synthesis of 1-((2R,3R,4R,5R)-4-(allyloxy)-3-fluoro-5-(hydroxymethyl)-3-methyltetrahydrofuran-2-yl)pyrimidin-2,4(1H,3H)-dione Compound of Formula (2') Wherein $R^{10}$ is allyl This example is representative of step j.i.3)

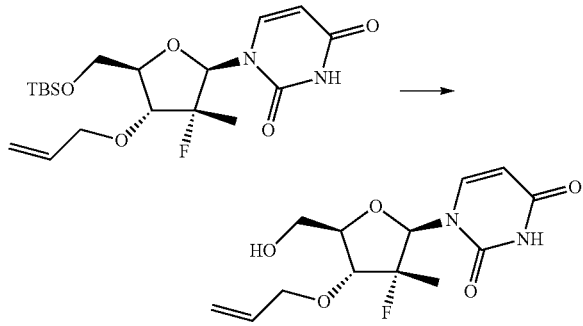

To a flask provided with mechanical stirrer, reflux condenser, thermometer and under nitrogen atmosphere are loaded 1-((2R,3R,4R,5R)-4-(allyloxy)-5-(((tert-butyldimethylsilyl)oxy)methyl)-3-fluoro-3-methyltetrahydrofuran-2-yl)pyrimidin-2,4(1H,3H)-dione prepared as described in example 21(800 mg, 1.9 mmol) and tetrahydrofuran (15 mL). To the solution thus obtained tetrabutylammonium fluoride (756 mg, 2.9 mmol) is added while keeping the mixture under stirring until the conversion is complete (about 1 hour). The product is concentrated to residue and purified by chromatographic column (eluent EtOAc) bringing to 268 mg of the desired product (yield: 47%).

$^1$H NMR (400 MHz, CDCl$_3$) δ 8.85 (s, 1H), 7.77 (d, J=8.0 Hz, 1H), 6.05 (d, J=18.8 Hz, 1H), 5.94-5.87 (m, 1H), 5.72 (d, J=8.0, 1H), 5.33-5.23 (m, 2H), 4.21-4.09 (m, 4H), 3.99-3.85 (m, 2H), 1.42 (d, J=22.0 Hz, 3H).

MS (ES): 323 (M+Na)$^+$.

Example 23

Synthesis of isopropyl ((((2R,3R,4R,5R)-3-(allyloxy)-5-(2,4-dioxo-3,4-dihydropyrimidin-1(2H)-yl)-4-fluoro-4-methyltetrahydrofuran-2-yl)methoxy)(phenoxy)phosphoryl)-L-alaninate Compound of Formula (3), Wherein $R^2$=allyl, $R^3$=uracil and $R^4$=hydrogen This example is representative of step a)

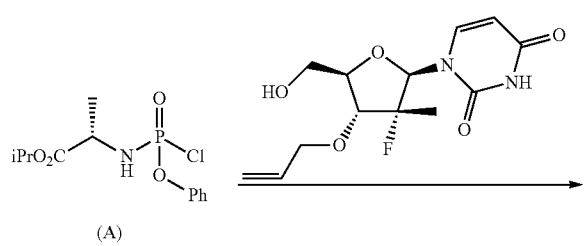

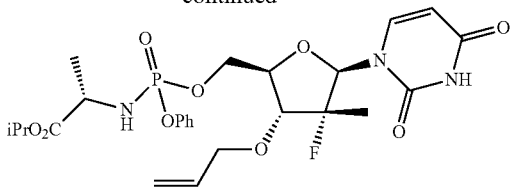

To a flask provided with mechanical stirrer, reflux condenser, thermometer and under nitrogen atmosphere are loaded 1-((2R,3R,4R,5R)-4-(allyloxy)-3-fluoro-5-(hydroxymethyl)-3-methyltetrahydrofuran-2-yl)pyrimidin-2,4 (1H,3H)-dione (10.0 g, 25.4 mmol) and tetrahydrofuran (140 mL). To the solution thus obtained and cooled to between −15 and −10° C. is added iso-propylmagnesium chloride complex 1:1 with lithium chloride (1.3 M in THF, 59 mL, 76.7 mmol), keeping the temperature below −5° C. When the addition is complete the reaction mixture is stirred between −20 and −10° C. for two hours and a solution of the phosphochloride (A) obtained as described in example 2 (17-18% w/w solution in MTBE, 120 g, 68.6 theoretical mmol) is added over about two hours, keeping the temperature below −10° C. Once the conversion is complete, the reaction mixture is poured, keeping the temperature below 5° C., on a mixture of isopropyl acetate (170 mL), water (90 mL) and acetic acid (4 mL) cooled to 0-5° C. It is heated to 20-25° C., then the phases are separated, the organic phase is washed with water and concentrated under vacuum to residue, moving the residual solvents by co-evaporation with methanol keeping the temperature below 40° C. 15.6 g of residue are obtained (quantitative yield).

HPLC analysis of the crude product (carried out by means of a Symmetry® C18 column (4.6 mm×25 mm, 5 μm) as eluent H$_2$O (+0.1% H$_3$PO$_3$)/CH$_3$CN 70:30 at 1 mL/min and UV 254 nm detector) shows a 95% conversion and a diastereomeric ratio of Sp:Rp=92:8.

$^1$H NMR (400 MHz, CDCl$_3$) δ 9.53 (s, 1H), 7.49 (d, J=8.0 Hz, 1H), 7.31-7.12 (nm, 5H), 6.08 (d, J=18.8 Hz, 1H), 5.89-5.83 (m, 1H), 5.64 (d. J=8.0 Hz, 1H), 5.31-5.19 (m, 2H), 4.99-4.95 (m, 1H), 4.99-4.95 (m, 1H), 4.55-4.51 (m, 1H), 4.35-4.31 (m, 1H), 4.19-3.76 (m, 5H), 1.40-1.11 (m, 12H).

MS (ES): 570 (M+H)$^+$, 592 (M+Na)$^+$.

Example 24

Synthesis of 1-((2R,3R,4R,5R)-5-(((tert-buthylidimethylsilyl)oxy)methyl)-3-fluoro-4-((4-methoxybenzyl)oxy)-3-methyltetrahydrofuran-2-yl)pyrimidin-2,4(1H,3H)-dione Compound of Formula (10), Wherein $R^7$ is tert-butyldimethylsilyl and $R^{10}$ is para-methoxybenzyl This example is representative of step j.i.2)

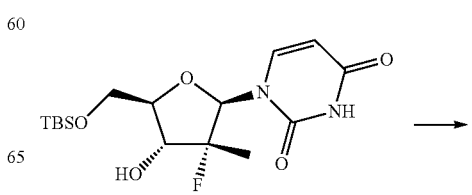

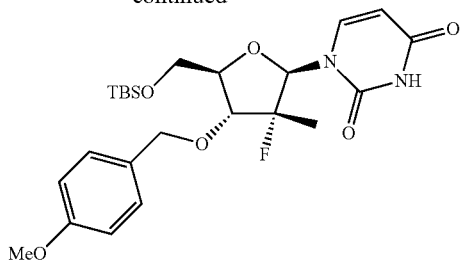
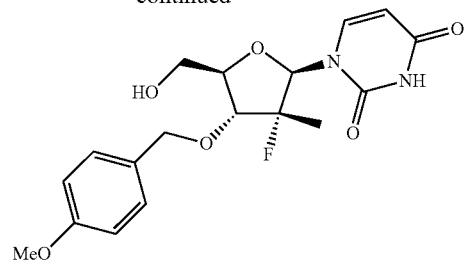

To a flask provided with mechanical stirrer, reflux condenser, thermometer and under nitrogen atmosphere are loaded 1-((2R,3R,4R,5R)-5-(((tert-buthyldimethylsilyl)oxy)methyl)-3-fluoro-4-hydroxy-3-methyltetrahydrofuran-2-yl)pyrimidin-2,4-(1H,3H)-dione prepared as described in *Tetrahedron* (2011), 67, 5487-5493 (1.6 g, 4.2 mmol) and tetrahydrofuran (18 mL). To the solution thus obtained and cooled to −10° C. is added 60% NaH in mineral oil (504 mg, 12.6 mmol), in subsequent portions and waiting for the effervescence to cease between an addition and the next one. The mixture is maintained at a temperature between −15 and −10° C. for 30 minutes, then para-methoxybenzyl chloride (570 μL, 4.2 mmol) is added drop-wise. When the addition is complete, temperature is left to raise to 25° C. and it is kept under stirring until the conversion is complete, monitored by TLC petroleum ether/EtOAc 7:3 (about 72 hours). The reaction mixture, cooled to 0° C., is diluted with ethyl acetate. Phases are separated and the aqueous phase is extracted with ethyl acetate; the organic phases are combined and dried over sodium sulphate, filtered and concentrated to residue under vacuum.

The product is purified by chromatographic column (using a gradient from petroleum ether alone to EtOAc alone) bringing to 415 mg of the desired product (yield: 20%).

$^1$H NMR (400 MHz, CDCl$_3$) δ 9.30 (s, 1H), 7.89 (d, J=8 Hz, 1H), 7.23 (d, J=8.4 Hz, 2H), 6.86 (d, J=8.4 Hz, 2H), 6.14 (d, J=17.6 Hz, 1H), 5.66 (d, J=8.0 Hz, 1H), 4.65-4.55 (m, 2H), 4.12-4.09 (m, 2H), 3.91-3.77 (m, 5H), 1.25 (d, J=22.0 Hz, 3H), 0.93 (s, 9H), 0.11 (s, 3H), 0.10 (s, 3H).

MS (ES): 495 (M+H)$^+$, 517 (M+Na)$^+$.

Example 25

Synthesis of 1-((2R,3R,4R,5R)-3-fluoro-5-(hydroxymethyl)-4-((4-methoxybenzyl)oxy)-3-methyl-tetrahydrofuran-2-yl)pyrimidin-2,4(1H, 3H)-dione Compound of Formula (2') Wherein R$^{13}$ is para-methoxybenzyl This example is representative of step j.i.3)

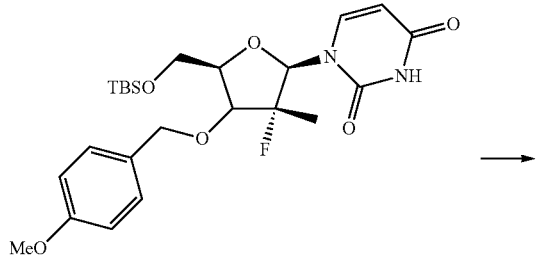

To a flask provided with mechanical stirrer, reflux condenser, thermometer and under nitrogen atmosphere are loaded 1-((2R,3R,4R,5R)-5-(((tert-buthyldimethylsilyl)oxy)methyl)-3-fluoro-((4-methoxybenz)oxy)-3-methyltetrahydrofuran-2-yl)pyrimidin-2,4(1H,3H)-dione prepared as described in example 24 (340 mg, 0.7 mmol) and tetrahydrofuran (10 mL). To the solution thus obtained tetrabutylammonium fluoride (270 mg, 1.0 mmol) is added while keeping the mixture under stirring until the conversion is complete (about 1 hour). The product is concentrated to residue and purified by chromatographic column (using a gradient from CHCl$_3$ alone to a CHCl$_3$/MeOH 90:10 mixture alone) bringing to 189 mg of the desired product (yield: 71%).

$^1$H NMR (400 MHz, CDCl$_3$) δ 7.85 (d, J=8.0 Hz, 1H), 7.22 (d, J=8.8 Hz, 2H), 6.81 (d, J=8.8 Hz, 2H), 6.03 (d, J=18.4 Hz, 1H), 5.63 (d, J=8.4 Hz, 1H), 4.62-4.55 (m, 2H), 4.03-3.86 (m, 3H), 3.73-3.65 (m, 4H), 1.19 (d, J=22.0 Hz, 3H).

MS (ES): 403 (M+Na)$^+$.

Example 26

Synthesis of isopropyl (((((2R,3R,4R,5R)-5-(2,4-dioxo-3,4-dihydropyrimidin-1(2H)-yl)-4-fluoro-3-((4-methoxybenzyl)oxy)-4-methyltetrahydrofuran-2-yl)methoxy)(phenoxy)phosphoryl)-L-alaninate Compound of Formula (3), Wherein R$^2$=para-methoxybenzyl, R$^3$=uracil e R$^4$=H This example is representative of step a)

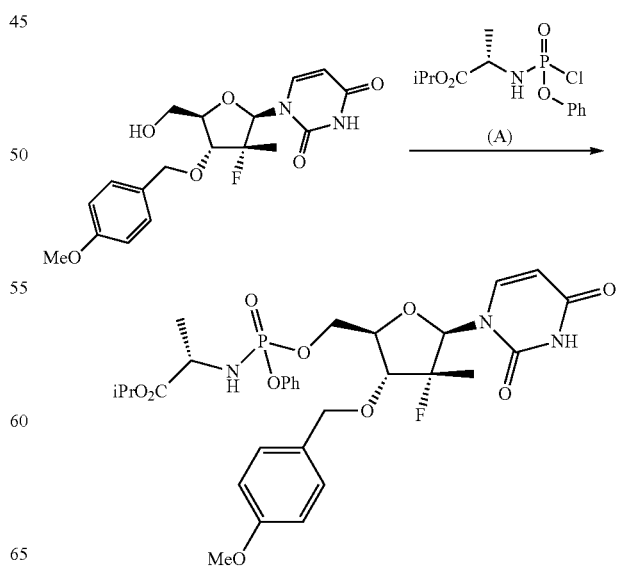

To a flask provided with mechanical stirrer, reflux condenser, thermometer and under nitrogen atmosphere are loaded 1-((2R,3R,4R,5R)-3-fluoro-5-(hydroxymethyl)-4-((4-methoxybenzyl)oxy)-3-methyltetrahydrofuran-2-yl)pyrimidin-2,4(1H,3H)-dione (10.0 g, 25.4 mmol) and tetrahydrofuran (140 mL). To the solution thus obtained and cooled to between −15 and −10° C. is added iso-propylmagnesium chloride complex 1:1 with lithium chloride (1.3 M in THF, 59 mL, 76.7 mmol), keeping the temperature below −5° C. When the addition is complete the reaction mixture is stirred between −20 and −10° C. for two hours and a solution of the phosphochloride (A) obtained as described in example 2 (17-18% w/w solution in MTBE, 120 g, 68.6 theoretical mmol) is added over about two hours, keeping the temperature below −10° C. Once the conversion is complete, the reaction mixture is poured, keeping the temperature below 5° C., on a mixture of isopropyl acetate (170 mL), water (90 mL) and acetic acid (4 mL) cooled to 0-5° C. It is heated to 20-25° C., then the phases are separated, the organic phase is washed with water and concentrated under vacuum to residue, moving the residual solvents by co-evaporation with methanol keeping the temperature below 40° C. 17.8 g of residue are obtained (quantitative yield).

HPLC analysis of the crude product (carried out by means of a Symmetry® C18 column (4.6 mm×25 mm, 5 μm) as eluent H$_2$O (+0.1% H$_3$PO$_3$)/CH$_3$CN 70:30 at 1 mL/min and UV 254 nm detector) shows a 97% conversion and a diastereomeric ratio of Sp:Rp=93:7.

$^1$H NMR (400 MHz, CDCl$_3$) δ 7.45 (d, J=7.6 Hz, 1H), 7.23-7.03 (m, 7H), ), 6.80 (d, J=8.0 Hz, 2H), 6.06 (d, J=18.8 Hz, 1H), 5.61 (d, J=7.6 Hz, 1H), 4.97-4.90 (m, 2H), 4.70-4.61 (m, 1H), 4.49-4.47 (m, 1H), 4.46-4.45 (m, 1H), 4.29-4.12 (m, 2H), 3.89-3.68 (m, 4H), 1.29-1.14 (m, 12H).

MS (ES): 650 (M+H)$^+$.

The invention claimed is:

1. A process for preparing a diastereomerically enriched mixture of the nucleoside phosphoramidate (4):

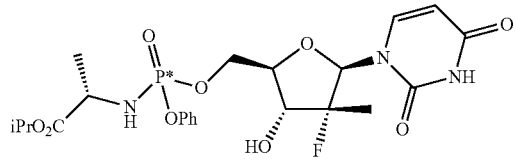

(4)

comprising the following synthesis steps:
a) phosphorylating the nucleoside (2) with a phosphoramidate (1) at a temperature of between −60 and 0° C. in an ethereal solvent or mixture of solvents;

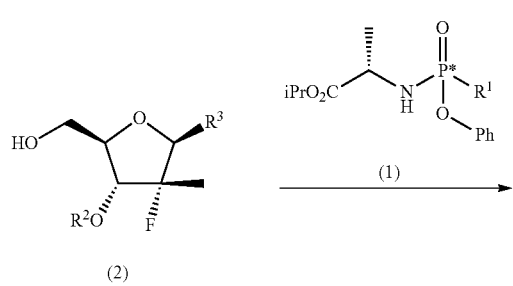

(2)

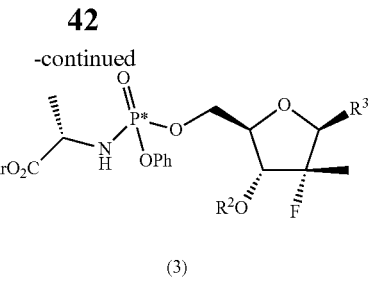

(3)

wherein:
the symbol "*" (asterisk) indicates a chiral center;
R$^1$ is chlorine, bromine, a sulfonate of formula —OSO$_2$R$^8$ or camphorsulfonate;
R$^2$ is an alcohol protecting group selected from carbonates or ethers;
R$^3$ is selected from

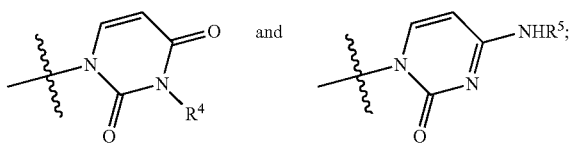

R$^4$ is hydrogen or an amine protecting group;
R$^5$ is hydrogen or an amine protecting group; and
R$^8$ is C1-C4 alkyl, aryl or aryl substituted with a C1-C4 alkyl, a halogen or a nitro group;
b) converting the nucleoside phosphoramidate (3) into the diastereomerically enriched mixture of the nucleoside phosphoramidate (4):

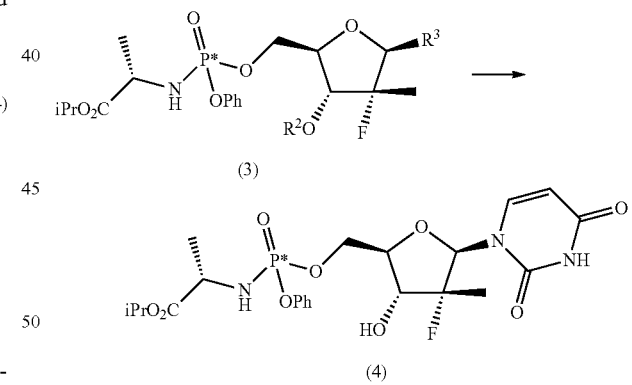

characterized in that
the reaction of step a) is carried out in the presence of an organomagnesium reagent and a halide of an alkaline metal, of zinc or of copper.

2. The process according to claim 1, wherein the organomagnesium reagent employed in step a) is iso-propylmagnesium chloride.

3. The process according to claim 1, wherein the halide employed in step a) is selected from the group consisting of lithium, sodium, potassium and cesium chloride.

4. The process according to claim 1, wherein the halide of an alkaline metal, of zinc or of copper is used in an amount ranging between 0.5 and 2 equivalents with respect to the amount of organomagnesium reagent.

5. The process according to claim 4, wherein the halide of an alkaline metal, of zinc or of copper is used in an amount of 1 equivalent with respect to the amount of organomagnesium reagent.

6. The process according to claim 1, wherein when $R^3$ is uracil, said process further comprising carrying out step b) according to a synthesis scheme comprising:

deprotecting the hydroxyl group in position 3' when $R^4$ is hydrogen; and deprotecting both the hydroxyl group in position 3' and the uracil nitrogen when $R^4$ is an amine protecting group.

7. The process according to claim 1, wherein $R^3$ is 4-aminouracil, said process further comprising carrying out step b) according to a synthesis scheme comprising:

deprotecting the hydroxyl group in position 3' and converting the 4-aminouracil into uracil when $R^5$ is hydrogen; and deprotecting both the hydroxyl group in position 3' and the nitrogen atom to which $R^8$ is bound, and also converting the 4-aminouracil into uracil when $R^5$ is an amine protecting group.

8. The process according to claim 1, further comprising a step C) wherein the diastereomerically enriched mixture of the nucleoside phosphoramidate (4) is transformed into a diastereomerically purified mixture of said phosphoramidate by crystallization from an alkylacetate, from a chlorinated solvent or a mixture thereof with acetonitrile or with an aliphatic hydrocarbon.

9. The process according to claim 1, wherein a nucleoside of formula (2'), nucleoside of formula (2) wherein $R^2$ is benzyl, para-methoxybenzyl or allyl, $R^3$ is uracil and $R^4$ is hydrogen, is prepared in an operation j) according to the synthesis scheme j.i), which comprises the following steps:

j.i.1) protecting the primary hydroxyl in position 5' of nucleoside (B):

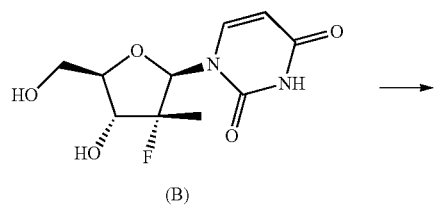

(B)

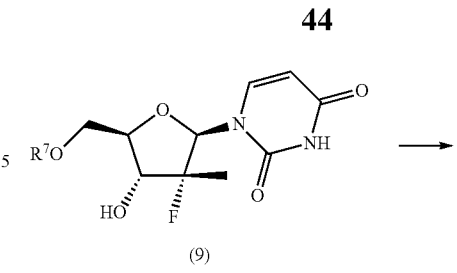

(9)

wherein $R^7$ is selected from a silyl ether or an ester;

j.i.2) selectively protecting the hydroxyl in position 3' of the protected nucleoside (9) to obtain the compound of formula (10):

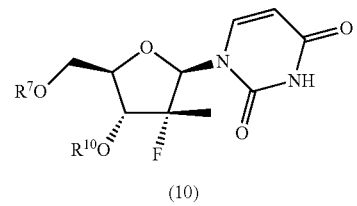

(10)

wherein $R^{10}$ is benzyl, para-methoxybenzyl or allyl;

j.i.3) removing the protecting group present on the primary hydroxyl in position 5' to obtain the nucleoside of formula (2'):

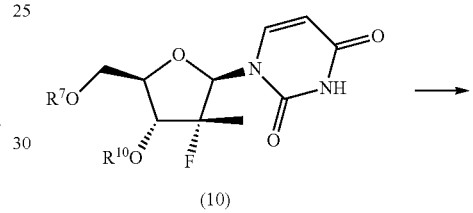

(10)

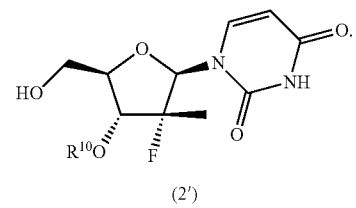

(2')

10. The process according to claim 1, wherein a nucleoside of formula (2'), nucleoside of formula (2) wherein $R^2$ is benzyl, para-methoxybenzyl or allyl, $R^3$ is uracil and $R^4$ is benzyl, para-methoxybenzyl or allyl, is prepared in an operation j) according to the synthesis scheme j.ii), which comprises the following steps:

j.ii.1) protecting the hydroxyl in position 5' of nucleoside (B):

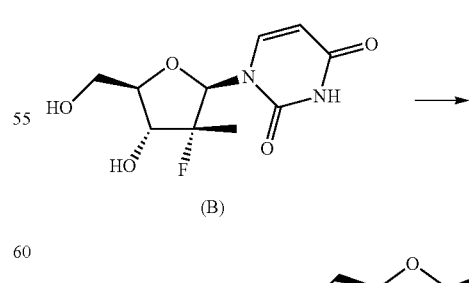

(B)

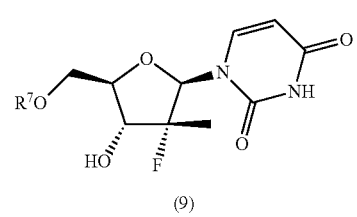

(9)

wherein R⁷ is selected from a silyl ether or an ester;

j.ii.2) converting the protected nucleoside (9) into the compound of formula (11):

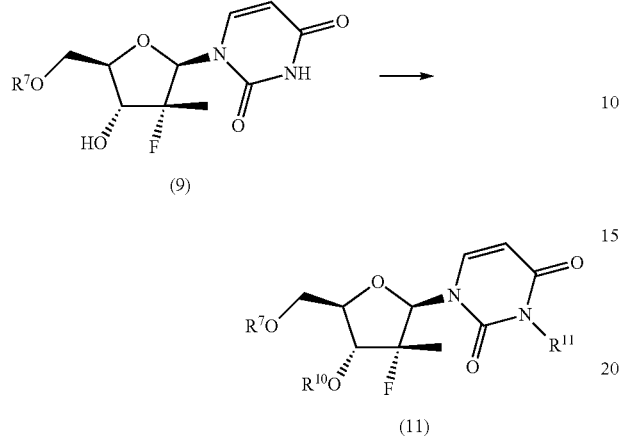

(9)

(11)

wherein R¹⁰ and R¹¹, each independently, are benzyl, para-methoxybenzyl or allyl;

j.ii.3) removing the protecting group present on the primary hydroxyl in position 5' to obtain the nucleoside of formula (2"):

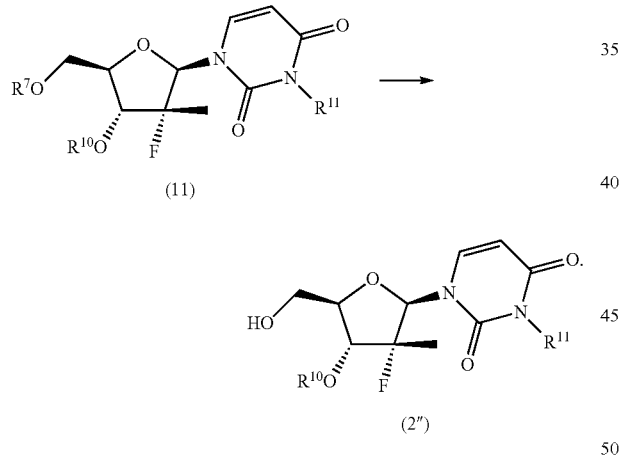

(11)

(2")

11. A process for preparing a diastereomerically purified mixture of the nucleoside phosphoramidate (4):

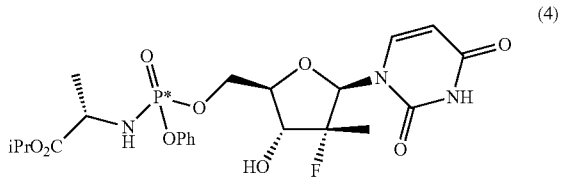

(4)

comprising the following synthesis steps:

d) preparing a diastereomerically purified form of the phosphoramidate (5):

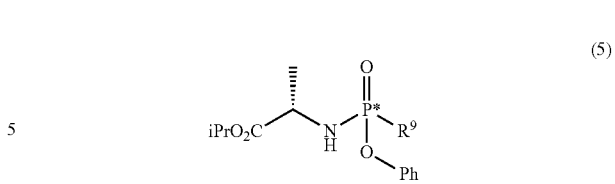

(5)

wherein R⁹ is an aryloxide substituted with at least one electron withdrawing group;

e) phosphorylating the nucleoside (6) with the diastereomerically purified form of the phosphoramidate (5) in the presence of an organomagnesium reagent and of an alkaline halide, a zinc halide, or a copper halide or a mixture thereof:

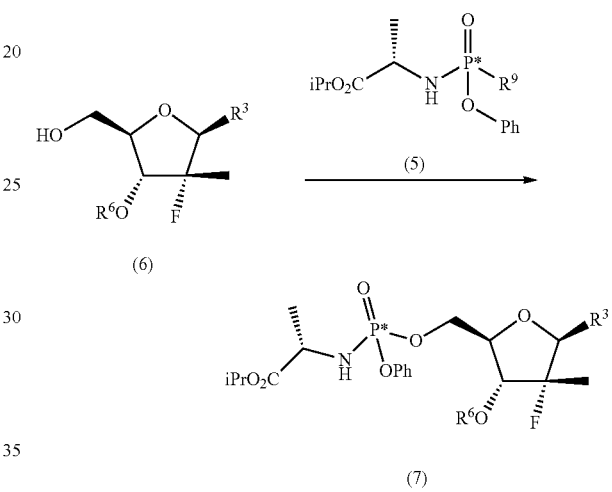

(6)

(7)

wherein:

the symbol "*" (asterisk) indicates a chiral center;

R³ is selected from

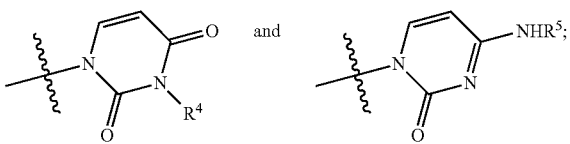

and

R⁴ is hydrogen or an amine protecting group;

R⁵ is hydrogen or an amine protecting group; and

R⁶ is hydrogen or an alcohol protecting group selected from carbonates or ethers;

f) if R⁴ and R⁶ are other than hydrogen and R³ is 4-aminouracil or a protected form thereof, converting the compound of general formula (7) into the diastereomerically purified mixture of the nucleoside phosphoramidate (4).

12. The process according to claim 11, wherein said diastereomerically purified form of phosphoramidate (5) is prepared in an operation h) comprising the following synthesis steps:

h.1) preparing the (L)-alanine isopropyl ester hydrochloride (Q):

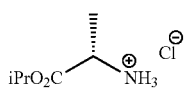

h.2) reacting the hydrochloride (Q) with phenyl dichlorophosphate in an alkylacetate, a chlorinated solvent, an ether or a mixture thereof in the presence of a base:

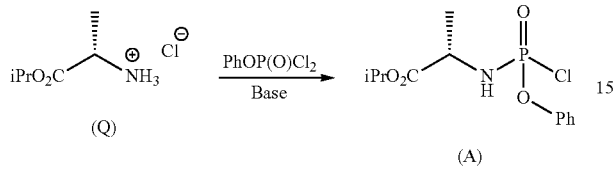

h.3) reacting the phosphochloride (A) with a phenol substituted with at least one electron withdrawing group (R⁹H) in an alkylacetate or a mixture thereof with a chlorinated solvent or an ether and in the presence of a base to prepare a diastereomerically enriched form of the phosphoramidate (5):

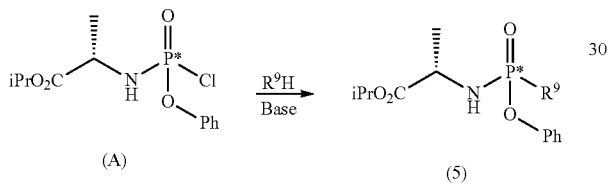

wherein $R^9$ is an aryloxide substituted with at least one electron withdrawing group;

h.4) isolating the diastereomerically purified form of phosphoramidate (5) by fractional crystallization.

13. A nucleoside having general formula (I):

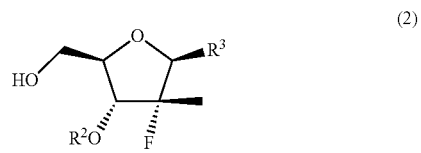

wherein:

$R^2$ is an alcohol protecting group selected from the group consisting of: benzyl, para-methoxybenzyl, allyl, 1-ethoxyethyl, methoxymethyl and para methoxybenzyloxymethyl;

$R^3$ is selected from the group consisting of:

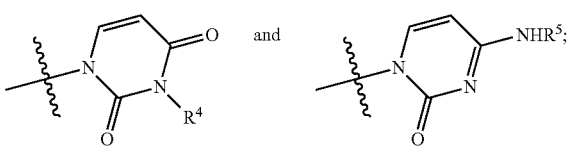

$R^3$ is selected from the group consisting of:

$R^4$ is hydrogen or an amine protecting group; and $R^5$ is hydrogen or an amine protecting group.

* * * * *